United States Patent
Nakanishi et al.

(10) Patent No.: US 9,949,635 B2
(45) Date of Patent: Apr. 24, 2018

(54) OPHTHALMIC SURGICAL APPARATUS AND ATTACHMENT FOR OPHTHALMIC SURGERY

(71) Applicant: KABUSHIKI KAISHA TOPCON, Itabashi-ku (JP)

(72) Inventors: Michiko Nakanishi, Katsushika-ku (JP); Takefumi Hayashi, Wako (JP); Hiroshi Akiyama, Soka (JP); Masahiro Akiba, Toda (JP); Makoto Fujino, Itabashi-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 15/306,586

(22) PCT Filed: Feb. 23, 2015

(86) PCT No.: PCT/JP2015/054997
§ 371 (c)(1),
(2) Date: Oct. 25, 2016

(87) PCT Pub. No.: WO2015/166695
PCT Pub. Date: Nov. 5, 2015

(65) Prior Publication Data
US 2017/0042419 A1    Feb. 16, 2017

(30) Foreign Application Priority Data
May 2, 2014   (JP) .................................. 2014-094981

(51) Int. Cl.
*A61B 3/14*    (2006.01)
*A61B 3/10*    (2006.01)
(Continued)

(52) U.S. Cl.
CPC ............ *A61B 3/102* (2013.01); *A61B 3/0008* (2013.01); *A61B 3/1025* (2013.01); *A61B 3/13* (2013.01);
(Continued)

(58) Field of Classification Search
USPC .................................................. 351/200–246
See application file for complete search history.

(56) References Cited

U.S. PATENT DOCUMENTS 5,493,109 A    2/1996   Wei et al.
5,795,295 A    8/1998   Hellmuth et al.
(Continued)

FOREIGN PATENT DOCUMENTS

JP    2000-235147 A    8/2000
JP    2001-133690 A    5/2001
(Continued)

OTHER PUBLICATIONS

International Search Report dated May 19, 2015 in PCT/JP2015/054997 filed Feb. 23, 2015.

*Primary Examiner* — Mohammed Hasan
(74) *Attorney, Agent, or Firm* — Oblon, McClelland, Maier & Neustadt, L.L.P.

(57) ABSTRACT

An ophthalmic surgical apparatus includes an observation optical system, an illumination optical system, an interference optical system, and an image forming unit. The observation optical system is configured to observe an eye through an objective lens. The illumination optical system is configured to illuminate the eye through the objective lens. The interference optical system includes a reference optical path and a signal optical path which leads to the eye through the deflecting member located between the objective lens and the eye, and is configured to detect interference light based on light having passed through the signal optical path (Continued)

and returning from the eye and the reference light having passed through the reference optical path. The image forming unit forms an image of the eye based on a detection result obtained by the interference optical system.

12 Claims, 11 Drawing Sheets

(51) Int. Cl.
| | | |
|---|---|---|
| *A61F 9/007* | (2006.01) | |
| *A61B 90/30* | (2016.01) | |
| *A61B 3/13* | (2006.01) | |
| *A61B 3/00* | (2006.01) | |
| *A61B 3/15* | (2006.01) | |
| *G02B 15/14* | (2006.01) | |
| *G02B 27/14* | (2006.01) | |

(52) U.S. Cl.
CPC ............... *A61B 3/14* (2013.01); *A61B 3/15* (2013.01); *A61B 90/30* (2016.02); *A61F 9/007* (2013.01); *G02B 15/14* (2013.01); *G02B 27/141* (2013.01)

(56) References Cited

U.S. PATENT DOCUMENTS

| | | | |
|---|---|---|---|
| 6,004,314 A | 12/1999 | Wei et al. | |
| 2012/0092615 A1* | 4/2012 | Izatt | A61B 3/102 351/206 |
| 2017/0215725 A1* | 8/2017 | Ishiai | A61B 3/102 351/206 |

FOREIGN PATENT DOCUMENTS

| | | |
|---|---|---|
| JP | 2006-95318 A | 4/2006 |
| JP | 3789960 B2 | 6/2006 |
| JP | 4091143 B2 | 5/2008 |

* cited by examiner

OPHTHALMIC SURGICAL APPARATUS AND ATTACHMENT FOR OPHTHALMIC SURGERY

TECHNICAL FIELD

Embodiments described herein relate generally to an ophthalmic surgical apparatus and an attachment for ophthalmic surgery.

BACKGROUND ART

Various surgeries are performed in the ophthalmic field. Cataract surgery and vitreoretinal surgery can be cited as typical examples thereof. An ophthalmic surgical apparatus is used in the surgery of the ophthalmic field. The ophthalmic surgical apparatus is used to observe an eye undergoing surgery illuminated by an illumination optical system with the naked eye through an observation optical system, capture and image of the eye, and the like.

Among such ophthalmic surgical apparatuses is the one that includes an optical coherence tomography (OCT) device for acquiring an OCT image of the eye undergoing surgery using OCT (e.g., Patent documents 1 to 3).

Patent Documents 1 to 3 each disclose an ophthalmic surgical apparatus having a configuration in which a beam combiner for acquiring an OCT image is arranged in the observation optical path between an objective lens and a zoom lens system. The beam combiner deflects, toward the objective lens, signal light for acquiring an OCT image of the eye undergoing surgery using OCT

PRIOR ART DOCUMENTS

Patent Documents

[Patent Document 1] Japanese Patent No. 3,789,960
[Patent Document 2] Japanese Patent No. 4,091,143
[Patent Document 3] Japanese Unexamined Patent Application Publication No. 2006-95318

SUMMARY OF THE INVENTION

Problems to be Solved by the Invention

In the ophthalmic surgical apparatus disclosed in Patent Documents 1 to 3, the beam combiner is arranged in the observation optical path between the zoom lens system and the objective lens. Accordingly, the light guided by the observation optical system (observation light) is attenuated, which influences an observation image of the eye such that the image becomes dark. Besides, in order to minimize the influence on the observation image, a new twist like the coating of the optical element is likely to be required.

Some ophthalmic surgical apparatuses are provided with a port for connecting an assistant's microscope or the like. The assistant's microscope is used by an assistant of the operator for observing an eye undergoing surgery. In this case, if the OCT optical system is connected to an existing port, another optical system cannot be connected to the port. Therefore, in addition to the existing port, it is required to add a new port to connect the OCT optical system.

The present invention has been made to solve the above problems, and the objects thereof are to provide an ophthalmic surgical apparatus and an attachment for ophthalmic surgery, capable of obtaining a high-quality observation image of the eye being observed and an OCT image without affecting the existing structure.

Means of Solving the Problems

According to one embodiment, an ophthalmic surgical apparatus includes: an observation optical system configured to observe an eye undergoing surgery through an objective lens; an illumination optical system configured to illuminate the eye through the objective lens; an interference optical system having a reference optical path and a signal optical path which leads to the eye through a deflecting member located between the objective lens and the eye, and configured to detect interference light based on light having passed through the signal optical path and returning from the eye, and reference light having passed through the reference optical path; and an image forming unit configured to form an image of the eye based on a detection result obtained by the interference optical system.

Effects of the Invention

According to at least one embodiment, an ophthalmic surgical apparatus is capable of acquiring a high-quality observation image and an OCT image without affecting the existing configuration. Further, an attachment for ophthalmic surgery is capable of obtaining a high-quality observation image and an OCT image without affecting the existing structure.

MODES FOR CARRYING OUT THE INVENTION

Figure 1:
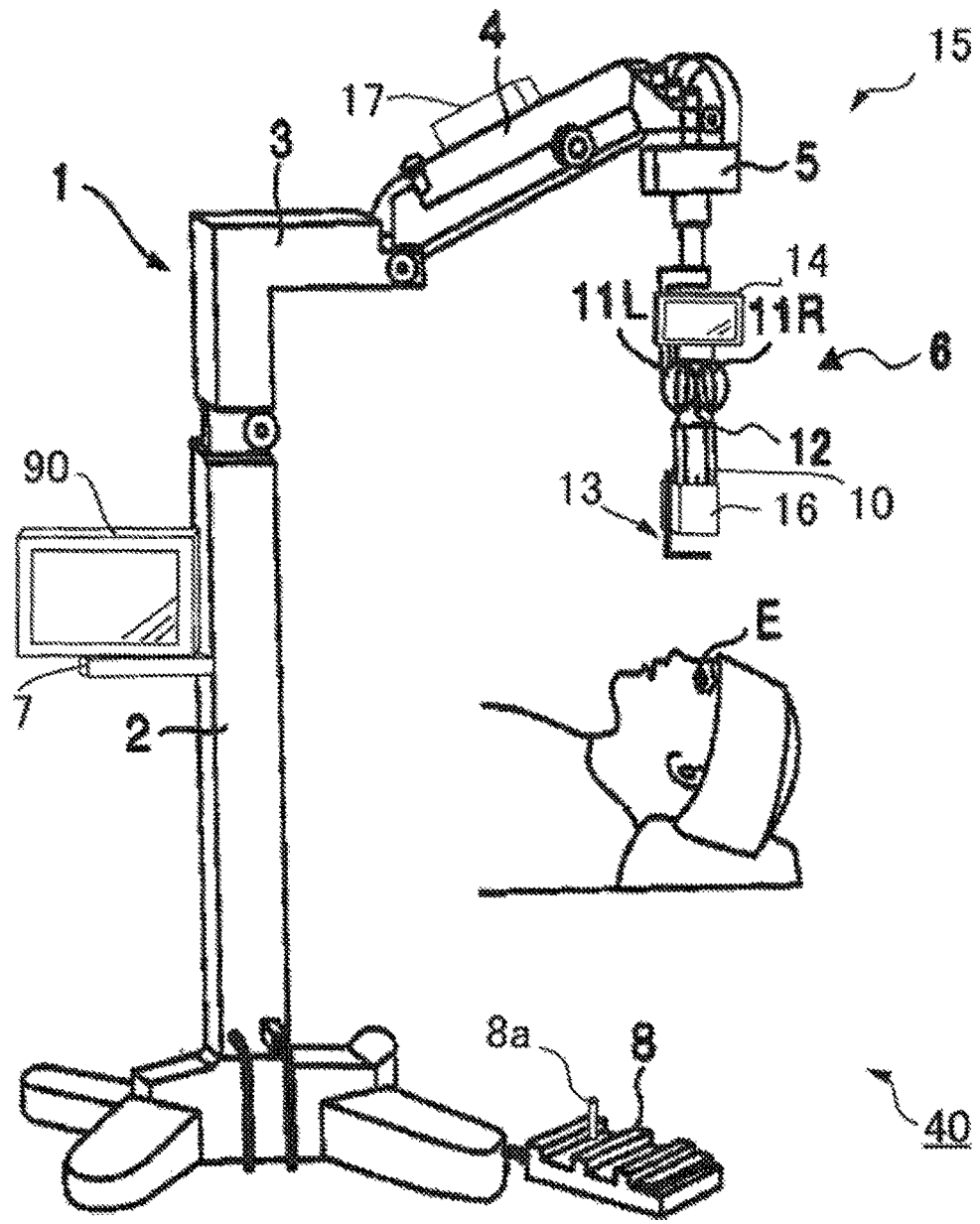
FIG. 1 is a schematic diagram illustrating an example of the exterior structure of an ophthalmic surgical apparatus according to an embodiment.

Referring now to the drawings, a description is given of exemplary embodiments of an ophthalmic surgical apparatus and an attachment for ophthalmic surgery according to the present invention. The ophthalmic surgical apparatus of the embodiments described below is used in ophthalmic surgery. With the ophthalmic surgical apparatus of the embodiments, an eye undergoing surgery (patient's eye) is illuminated by an illumination optical system so that the reflected light is incident on an observation optical system, thereby an observation image of the eye is acquired. The attachment for ophthalmic surgery is configured to be detachably attached to an ophthalmic observation apparatus that can be used in ophthalmic surgery.

In the following embodiments, an ophthalmic surgical system is configured to acquire an OCT image of an eye undergoing surgery when an attachment (first optical unit) including at least part of the OCT optical system is attached to an ophthalmic surgical microscope (main body). Incidentally, any site of the eye may be photographed. Examples of the site to be imaged may include the cornea, the vitreous body, the crystalline lens, the ciliary body, and the like in the anterior eye segment, and may also include the retina, choroid, vitreous body, and the like in the posterior eye segment. In addition, a peripheral portion of the eye, such as an eyelid and an eye socket, may be imaged. A sectional image or a three-dimensional image of the eye can be formed based on return light of signal light having passed through the attachment by using a known technique. Images acquire through OCT may be herein collectively referred to as OCT images. Similarly, measurement operation (measurement action) for forming an OCT image may be herein referred to as OCT measurement. Incidentally, the contents of documents cited herein may be incorporated by reference in the following embodiments.

In the following embodiments, a description is given of the configuration that employs Fourier domain OCT. In particular, an ophthalmic surgical apparatus of the embodiments can acquire an OCT image of the eye using a technique known as swept source OCT.

The configuration of the embodiments can be applied to ophthalmic surgical apparatuses using OCT of other types than swept source OCT such as spectral domain OCT. While the following embodiments describe an apparatus obtained by combining an OCT device including an OCT optical system and an ophthalmic surgical microscope, the OCT device having the configuration of the embodiments can be combined with other ophthalmic observation apparatuses than the ophthalmic surgical microscope. Examples of the other ophthalmic observation apparatuses include a scanning laser ophthalmoscope (SLO), a slit lamp microscope, a fundus camera, and the like.

First Embodiment

Exterior Structure

FIG. 1 illustrates the exterior structure of an ophthalmic surgical apparatus according to the first embodiment. An ophthalmic surgical apparatus 40 includes an ophthalmic surgical microscope 1 and an OCT device 15. The ophthalmic surgical microscope 1 includes a support post 2, a first arm 3, a second arm 4, a drive unit 5, a microscope 6, a support portion 7, a foot switch 8, and a display 90. The microscope 6 includes an illumination optical system configured to illuminate an eye E undergoing surgery, and an observation optical system configured to form an observation image from illumination light which has been emitted by the illumination optical system and reflected from the eye E.

The OCT device 15 includes an interference optical system and an image forming unit. The interference optical system splits the light emitted from a light source into signal light and reference light, and detects interference light. The interference light is generated on the basis of the signal light that has propagated through a signal optical path (which is an optical path for the signal light) and returning from the eye E and the reference light that has passed through a reference optical path (which is an optical path for the reference light). The image forming unit is configured to form an OCT image based on the interference light detected. The OCT device 15 includes a first optical unit 16 and a second optical unit 17. One or both of these two units houses an optical element for forming an OCT image and the like. The first optical unit 16 is detachably attached to the microscope 6. The second optical unit 17 is arranged in the upper portion of the second arm 4 that supports the microscope 6. The first optical unit 16 and the second optical unit 17 are connected by an optical fiber (light guide).

A mechanism is provided between the first arm 3 and the second arm 4. The mechanism is configured to move the second arm 4 three-dimensionally with respect to the first arm 3. Further, a mechanism that makes the microscope 6 rotatable in the horizontal direction as required may be provided to a portion where the microscope 6 is attached to the arm extending downward from the drive unit 5. Such mechanisms and the drive unit 5 correspond to the mechanism for changing the position and/or orientation of the microscope 6 (main body). Generally, the operator (surgeon) performs surgery locating on the side of the top of the head or the ear of the patient. The microscope 6 is arranged above the eye E in a state with its eyepiece facing the operator. The "orientation of the microscope 6" may include a concept representing the orientation of the eyepiece with respect to the patient, the orientation of the eyepiece with respect to the optical axis of the optical system (e.g., the optical axis of an objective lens), the operator's location with respect to the patient, and the like.

The drive unit 5 includes an actuator such as a motor. The drive unit 5 is configured to move the microscope 6 in the vertical direction and the horizontal direction in response to operation performed by using an operating lever 8a of the foot switch 8. With this, the microscope 6 is movable three-dimensionally.

The microscope 6 has a barrel portion 10 that houses various types of optical systems, various types of drive systems, and the like. The barrel portion 10 is provided with an inverter unit 12 in its upper portion. When an observation image of the eye E is obtained as an inverted image, the inverter unit 12 converts the observation image into an erect image. The inverter unit 12 is provided with a pair of right and left eyepieces 11R and 11L in its upper portion. An observer (operator, etc.) can have a binocular vision of the eye E undergoing surgery by looking into the right and left eyepieces 11R and 11L.

The first optical unit 16 is detachably attached to the microscope 6 (the barrel portion 10). The first optical unit 16 is an attachment for storing at least part of the interference optical system. In this embodiment, the first optical unit 16 includes at least a deflecting member. The deflecting member is configured to deflect signal light for acquiring an OCT image in the direction toward the eye E. The microscope 6 is an example of the "main body".

A front lens 13 is connected to the microscope 6 through a holding arm. The front lens 13 is configured to be detachably attached to a position on the optical axis of the objective lens which is located at the lower end of the barrel portion 10. In particular, during the observation of the eye E undergoing surgery, the front lens 13 can be located in a position between the front focal position of the objective lens and the eye E. The front lens 13 converges the illumination light to illuminate the inside of the eye E (posterior eye segment such as the retina, the vitreous body, and the like). A plurality of lenses having different refractive powers (e.g., 40D, 80D, 120D, etc.) are prepared as the front lens 13, and one of them is selectively used.

An intraoperative observation monitor 14 is arranged on the top of the barrel portion 10. The intraoperative observation monitor 14 displays, for example, an observation image as a moving image and an OCT image as a live image. The moving image of the observation image and the live image of the OCT image may be acquired by the OCT device 15. Incidentally, the moving image of the observation image may be acquired by the ophthalmic surgical microscope 1. Besides, the intraoperative observation monitor 14 may also display any information that can be referred to during surgery, such as information acquired by preoperative diagnosis, past surgery, or the like. Such information can be acquired from, for example, an in-hospital system such as an electronic medical record system, an image archiving system, or the like, via a network such as LAN. The intraoperative observation monitor 14 may be configured to be detachable, and further it may be a general-purpose tablet terminal.

The support post 2 is configured to support the support portion 7. The support portion 7 is configured to support the display 90 such that the orientation of the screen can be varied in a desired direction. The display 90 displays, for example, an OCT image (still image) acquired by the OCT device 15 that captures a live image. The display 90 can also display any image acquired by the ophthalmic surgical microscope 1 or the OCT device 15. Further, the display 90 may also display any information that can be referred to during surgery, such as information acquired by preoperative diagnosis, past surgery, or the like. Note that the display 90 and the intraoperative observation monitor 14 may be provided with an operation unit that allows the same operation as the foot switch 8.

With this configuration, the operator can perform surgery while observing the cross-sectional image of the site undergoing surgery during the surgery.

Configuration

Ophthalmic Surgical Microscope

Figure 2:
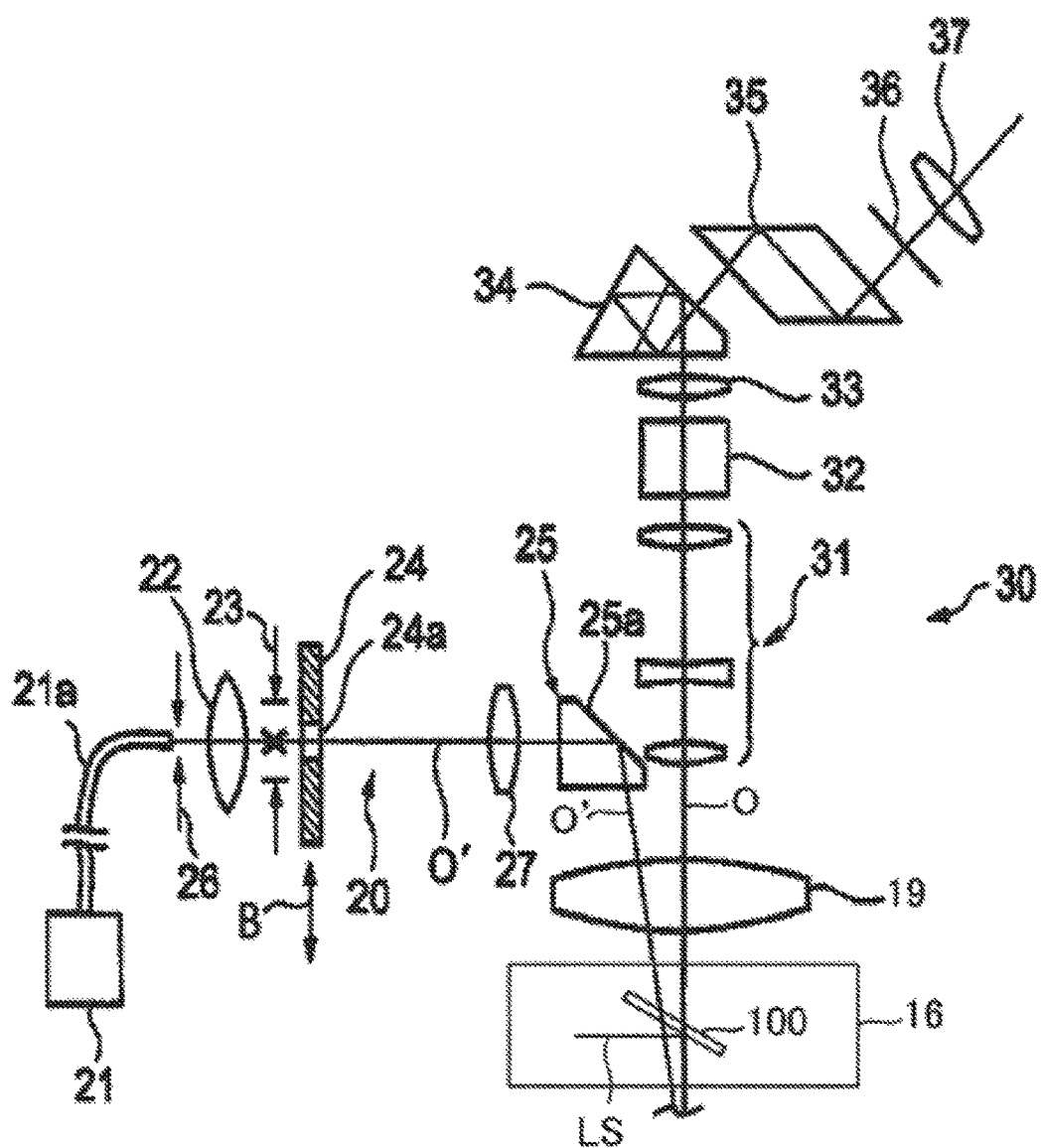
FIG. 2 is a schematic diagram illustrating an example of the configuration of an optical system of the ophthalmic surgical apparatus according to the embodiment.
Figure 3:
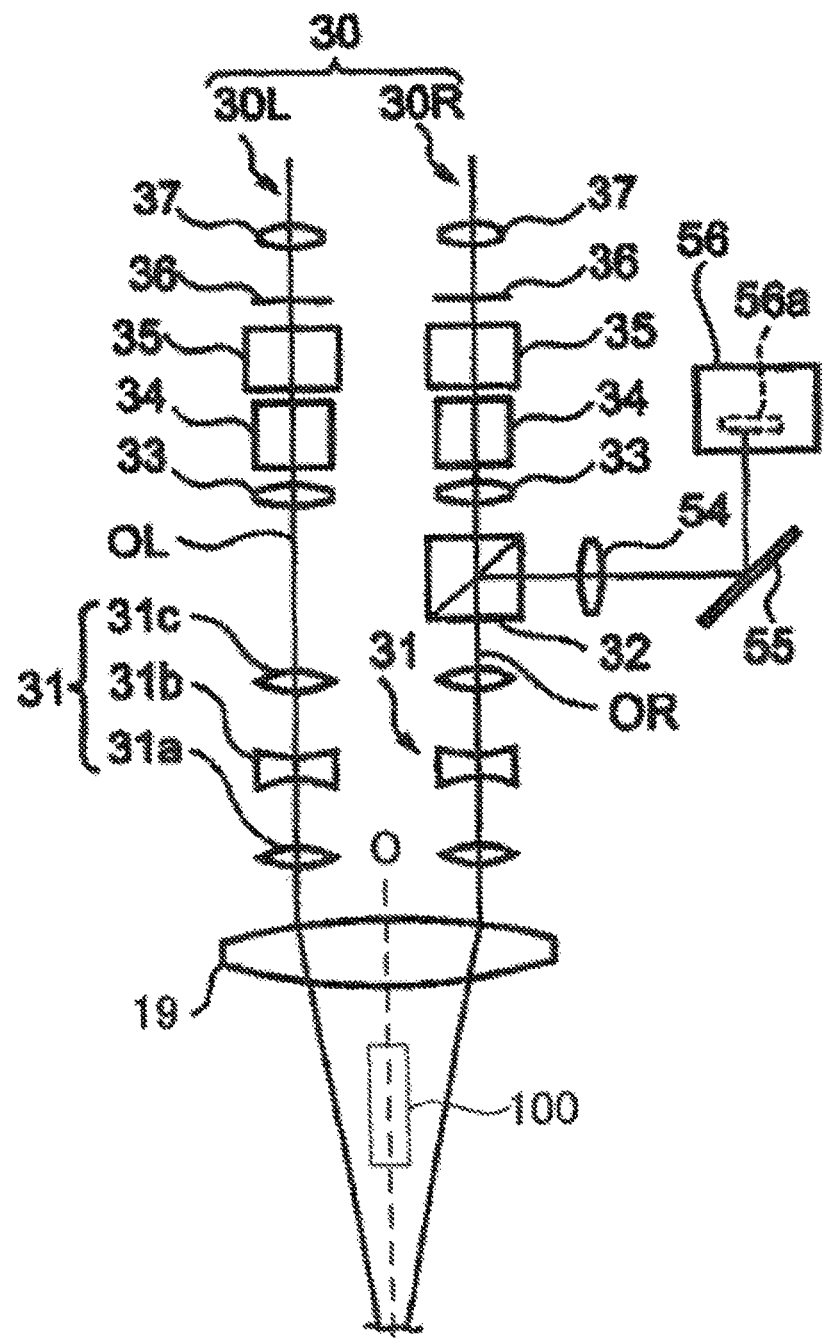
FIG. 3 is a schematic diagram illustrating an example of the configuration of an optical system of the ophthalmic surgical apparatus according to the embodiment.

FIGS. 2 and 3 illustrate an optical system of the ophthalmic surgical microscope 1. FIG. 2 illustrates the optical system as viewed from the left side of the operator. FIG. 3 illustrates the optical system as viewed from the operator's side. In addition to the configuration illustrated in FIGS. 2 and 3, it is also possible to provide an optical system for operator's assistant (assistant's microscope) to observe the eye E undergoing surgery. FIGS. 2 and 3 also illustrate a deflecting member 100 housed in the first optical unit 16. The deflecting member 100 is a member for deflecting the signal light from outside of the optical system of the ophthalmic surgical microscope 1 in the direction toward the eye E.

In this embodiment, terms such as up, down, left, right, front back, and the like indicate directions as viewed from the operator's side unless otherwise noted. Regarding up and down directions, the direction from an objective lens 19 toward the observation object (the eye E) is referred to as down, and the direction opposite thereto is referred to as up. In general, the patient undergoes surgery in the supine position. Therefore, the up and down direction corresponds to the vertical direction.

The optical system of the ophthalmic surgical microscope 1 includes an illumination optical system 20 and an observation optical system 30.

As illustrated in FIG. 3, a pair (left and right) of the observation optical system 30 is provided. The observation optical system 30 on the left is referred to as a left observation optical system 30L and the observation optical system 30 on the right is referred to as a right observation optical system 30R. Reference sign OR represents the optical axis of the right observation optical system 30R (observation optical axis), while reference sign OL represents the optical axis of the left observation optical system 30L (observation optical axis). The right and left observation optical systems 30R and 30L are arranged such that the optical axis O of the objective lens 19 is located between them (see FIG. 2).

The right and left observation optical systems 30R and 30L each include a zoom lens system 31, an imaging lens 33, an image erecting prism 34, an interpupillary adjustment prism 35, a field diaphragm 36, and an eyepiece 37. The right observation optical system 30R further includes a beam splitter 32.

The zoom lens system 31 includes a plurality of zoom lenses 31a, 31b, and 31c. Each of the zoom lenses 31a to 31c is movable in a direction along the observation optical axis OL (or the observation optical axis OR) by a zoom mechanism (not illustrated). This enables a change in the magnification for observing or photographing the eye E.

The beam splitter 32 of the right observation optical system 30R separates a part of observation light guided along the observation optical axis OR from the eye E to guide it to an imaging optical system. The imaging optical system includes an imaging lens 54, a reflecting mirror 55, and a video camera 56.

The video camera 56 includes an image pickup device 56a. The image pickup device 56a may be formed of, for example, a charge coupled device (CCD) image sensor, a complementary metal-oxide-semiconductor (CMOS) image sensor, or the like. A device having a two-dimensional light receiving surface (area sensor) is used as the image pickup device 56a.

In the use of the ophthalmic surgical microscope 1, the light receiving surface of the image pickup device 56a is located in, for example, a position optically conjugate with the surface of the cornea of the eye E, or a position optically conjugate with a position distant in the depth direction from the apex of the cornea by a half of the corneal curvature radius.

The image erecting prism 34 converts an indirect image to an erect image. The interpupillary adjustment prism 35 is an optical element for adjusting the distance between right and left observation light beams according to the eye width of the operator (the distance between the left and right eyes). The field diaphragm 36 shields peripheral areas in the cross section of the observation light to limit the field of view of the operator.

As illustrated in FIG. 2, the illumination optical system 20 includes an illumination light source 21, an optical fiber 21a, an emission diaphragm 26, a condenser lens 22, an illumination field diaphragm 23, a slit plate 24, a collimator lens 27, and an illumination prism 25.

The illumination field diaphragm 23 is located in a position optically conjugate with the front focal position of the objective lens 19. The slit plate 24 has slit holes 24a, which is formed in a position optically conjugate with the front focal position.

The illumination light source 21 is located outside of the lens barrel portion 10 of the microscope 6. One end of the optical fiber 21a is connected to the illumination light source 21. The other end of the optical fiber 21a is arranged at a position facing the condenser lens 22 in the lens barrel portion 10. Illumination light output from the illumination light source 21 is guided through the optical fiber 21a to enter the condenser lens 22.

The emission diaphragm 26 is provided in a position facing the emission end of the optical fiber 21a (fiber end on the condenser lens 22 side). The emission diaphragm 26 functions to shield a partial region of the emission end of the optical fiber 21a. The emission region of the illumination light can be changed by changing the area shielded by the emission diaphragm 26. This enables the projection angle of the illumination light to be changed. That is, the angle between the direction of the illumination light incident on the eye E and the optical axis O of the objective lens 19, or the like can be changed.

The slit plate 24 is formed of a disk-shaped member having light shielding properties. The slit plate 24 is provided with the plurality of slit holes 24a that constitute a light transmitting portion having a shape corresponding to the shape of a reflecting surface 25a of the illumination prism 25. The slit plate 24 is configured to be moved by a drive mechanism (not illustrated) in directions perpendicular to the illumination optical axis O' (directions indicated by a double-headed arrow B in FIG. 2) With this, the slit plate 24 is inserted into and removed from the illumination optical axis O'.

The collimator lens 27 collimates the illumination light having passed through the slit hole 24a into a parallel light beam. The illumination light that has become a parallel light beam is reflected by the reflecting surface 25a of the illumination prism 25 and is projected onto the eye E via the objective lens 19. The illumination light is projected onto the eye E is (partly) reflected by the cornea. The illumination light reflected by the eye E (sometimes referred to as observation light) is incident on the observation optical system 30 via the objective lens 19. With this configuration, an enlarged image of the eye E can be observed.

In this embodiment, when the first optical unit 16 is attached to the barrel portion 10 of the microscope 6, the deflecting member 100, which is housed in the first optical unit 16, is located between the objective lens 19 and the eye E. Specifically, the deflecting member 100 is arranged at a distance d (here, d≥0) perpendicular to the optical axis O from a predetermined position on the eye E side in the optical axis O of the objective lens 19. The deflecting member 100 is arranged out of the optical path (observation optical path) formed by the observation optical system 30. In this embodiment, the deflecting member 100 is arranged in a position out of both the observation optical axis OL and the observation optical axis OR, and is located on the optical axis O of the objective lens 19. Part of the deflecting member 100 may be located in the observation optical path, the optical path formed by the illumination optical system 20 (illumination optical path), or the like. In the case where the deflecting member 100 is arranged in the illumination optical path, the intensity of the illumination light can be controlled to make up for the attenuation of the observation light. Therefore, if the brightness of an acquired image is not important or if the illumination light can be controlled, the deflecting member 100 may be arranged in the illumination optical path. On the other hand, in the case where the deflecting member 100 is arranged in the observation optical path, the brightness of a photographed image and an image observed with the naked eye is reduced due to the attenuation of the observation light, which may adversely affect the observation of the eye E. Therefore, it is desirable that the deflecting member 100 is arranged so as not to enter the observation optical path as much as possible. The deflecting member 100 includes a beam splitter, a half mirror or a dichroic mirror.

The observation optical system 30 is an example of the "observation optical system" of the embodiment. The illumination optical system 20 is an example of the "illumination optical system" of the embodiment.

OCT Device

Figure 4:
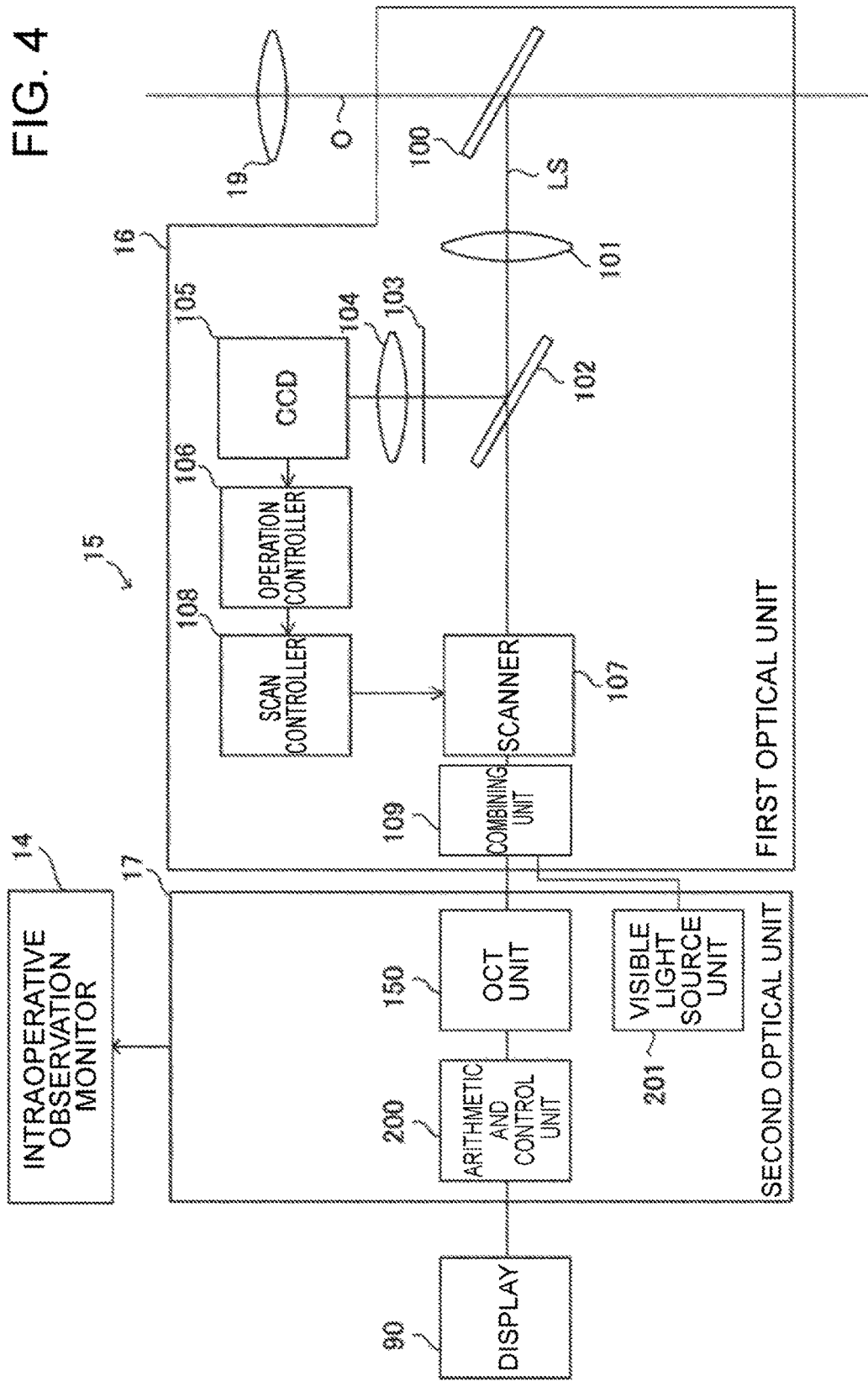
FIG. 4 is a schematic diagram illustrating an example of the configuration of an OCT device of the ophthalmic surgical apparatus according to the embodiment.

FIG. 4 is a block diagram illustrating an example of the configuration of the OCT device 15. In FIG. 4, like reference symbols designate like parts as in FIG. 1, and the explanation thereof is omitted as appropriate. FIG. 4 also illustrates the objective lens 19 and the optical axis O thereof.

In this embodiment, in order that the operator may identify the scan position of the signal light for OCT measurement without separating his/her eye from the eyepiece, aiming light, which is visible light, can be irradiated to the eye E together with the signal light. Further, by obtaining a visible image (an image captured using visible light) at the same time as the projection of the aiming light onto the eye E, the scan position of the signal light can be checked with an image displayed. In the case where a configuration excluding the observation of the scan position of the signal light through the eyepiece (i.e., with the naked eye) is applied, invisible light (infrared light, etc.) can be used as the aiming light. Besides, when the aiming light made of visible light is used, the trajectory of the aiming light may be specified from an invisible image (an image captured using invisible light) such that an image indicating the position and orientation of the trajectory is presented in an image (visible image, etc.) acquired separately or in the field of view of the naked eye observation.

The first optical unit 16 is formed as a detachable attachment for the microscopes 6 that holds at least the objective lens 19. In this embodiment, the first optical unit 16 includes the deflecting member 100 described above, a focus lens 101, a beam splitter 102, a filter 103, a condenser lens 104, a CCD image sensor 105, an operation controller 106, a scanner 107, a scan controller 108, and a combining unit 109. The first optical unit 16 need not necessarily include all of the above members. For example, it may be sufficient if the first optical unit 16 includes at least the deflecting member 100 and the scanner 107. In addition, for example, another unit than the first optical unit 16 (e.g., the second optical unit 17) may include the operation controller 106. It is also possible to employ the configuration in which the arithmetic and control unit (arithmetic and control processor) provided in the ophthalmic surgical microscope 1 bears at least a part of the functions of the operation controller 106.

The second optical unit 17 includes an OCT unit 150, an arithmetic and control unit 200, and a visible light source unit 201. Another unit than the second optical unit 17 (e.g., the first optical unit 16) may include the visible light source unit 201. The display 90 is connected to the second optical unit 17. Further, the intraoperative observation monitor 14 (see FIG. 1) is also connected to the second optical unit 17.

While the deflecting member 100 is arranged on the optical axis O of the objective lens 19 such that it is arranged out of the observation optical path, it may be located in a position out of at least one of the observation optical path and the illumination optical path. The deflecting member 100 may be a beam splitter (half mirror) arranged on at least one of the observation optical path and the illumination optical path. The deflecting member 100 is configured to deflect the signal light guided along the signal optical path in the direction toward the eye E as well as deflecting the signal light returning from the eye E in the direction toward the focus lens 101.

In this embodiment, a moving image is acquired based on a detection signal obtained by the CCD image sensor 105 in the first optical unit 16. The moving image is captured using, for example, infrared light or red-free light. Here, the red-free light is obtained by removing a red component from visible light.

When the infrared light is used in photography, for example, a component for projecting the infrared light onto the eye E is provided around the front lens 13, and a dichroic mirror is employed as the deflecting member 100. In this case, the deflecting member 100 reflects, from among the light reflected from the eye E, at least light in the wavelength bands used for OCT measurement and the wavelength bands of the infrared light, while transmitting light for observation that is light in the wavelength bands of visible light. Incidentally, the component for projecting the infrared light includes, for example, at least one infrared light emitting diode (LED). The component for projecting the infrared light need not necessarily be located in the periphery of the front lens 13. The component for projecting the infrared light may be arranged around the objective lens 19, between the objective lens 19 and the eye E, or the like. A half mirror may also be used as the deflecting member 100.

When the red-free light is used in photography, a half mirror is employed as the deflecting member 100.

The combining unit 109, the scanner 107, the beam splitter 102, and the focus lens 101 are arranged in the optical path for OCT measurement in this order from the OCT unit 150 side.

The combining unit 109 is connected to the OCT unit 150 via an optical fiber. The combining unit 109 is also connected to the visible light source unit 201 via an optical fiber. The visible light source unit 201 outputs aiming light including visible light (e.g., light with center wavelength of 633 nm). The aiming light output from the visible light source unit 201 is guided to the combining unit 109. The signal light for OCT measurement output from the OCT unit 150 (e.g., light with center wavelength of 1050 nm) is guided to the combining unit 109. The combining unit 109 combines the optical path for OCT measurement with the optical path of the aiming light. That is, the combining unit 109 combines the optical path of the visible light output from the visible light source unit 201 with the signal optical path at a location between the splitting unit and the scanner 107. The combining unit 109 may be formed of a fiber coupler. The combining unit 109 is an example of the "combining unit" of the embodiment. In the following, the optical path formed by combining the optical paths through the combining unit 109 is also described as a new optical path for OCT measurement.

Note that by employing a configuration in which the signal light for OCT measurement returning from the eye E is prevented from entering the visible light source unit 201, it is possible to prevent a reduction in the detection efficiency of the signal light for OCT measurement.

Combined light generated by the combining unit 109 is collimated into a parallel beam by a collimator (not illustrated), and incident on the scanner 107. The scanner 107 changes the traveling direction of light (signal light) passing through the optical path for OCT measurement. Thereby, the eye E undergoing surgery can be scanned by the signal light. The scanner 107 includes, for example, a galvanometer mirror that scans the signal light in the x direction, a galvanometer mirror that scans in the y direction perpendicular to the x direction, and a mechanism(s) for driving the galvanometer mirrors independently. Thereby, the signal light can be scanned in an arbitrary direction on the xy plane.

The scanner 107 also changes the traveling direction of the aiming light guided through the signal optical path. Thereby, the aiming light can be irradiated to the eye E. With the configuration of the scanner 107 as described above, the aiming light can be deflected in an arbitrary direction on the xy plane. The time for irradiating the aiming light (the time when the user can visually recognize the range (area) of OCT scan) is not only during OCT measurement, but also when setting an range of OCT scan, when checking the area to which OCT scan has been applied, or the like.

The scanner 107 may be realized by a known optical scanner. The scanner 107 is an example of the "scanner".

Through the beam splitter 102, an optical path for tracking branches from the optical path for OCT measurement. Specifically, through the beam splitter 102, the optical path for tracking branches from the optical path of the signal light for OCT measurement returning from the eye E. The filter 103, the condenser lens 104, and the CCD image sensor 105 are arranged in the optical path for tracking in this order from the beam splitter 102 side.

In the case where infrared photography is performed using the CCD image sensor 105 while the infrared light and visible light are being irradiated to the eye E, the filter 103 has filter characteristics to transmit the infrared light. Thereby, the light having passed through the optical path for tracking branched by the beam splitter 102 transmits through the filter 103 to become the infrared light. On the other hand, in the case where infrared photography is performed using the CCD image sensor 105 while the infrared light is being irradiated to the eye E, the light having passed through the optical path for tracking branched by the beam splitter 102 is directly incident on the CCD image sensor 105 (i.e., the filter 103 is not required). Incidentally, in this case, the beam splitter 102 is configured to transmit light of wavelength bands corresponding to the signal light, and reflect light with wavelength bands of the infrared light for tracking. As a specific example, using the signal light with wavelengths longer than the infrared light for tracking, a beam splitter (dichroic mirror) having characteristics to separate them from one another is employed as the beam splitter 102.

Further, in the case where red-free photography is performed using the CCD image sensor 105 while the visible light is being irradiated to the eye E, the following configurations may be selectively applied according to the case where the aiming light is not projected onto the eye E and the case where the aiming light is projected onto the eye E.

In the case where the aiming light is not projected onto the eye E, the filter 103 has filter characteristics for the blocking red components contained in the visible light. With this, the visible light passing through the optical path for tracking branched by the beam splitter 102 transmits through the filter 103 and become red-free light. Incidentally, a light source capable of outputting red-free light may be used. In this case, red-free photography is performed using the CCD image sensor 105 while the red-free light is being irradiated to the eye E. In this case, the filter 103 is not required.

In contrast, in the case where the aiming light is projected onto the eye E, a half mirror is employed for the deflecting member 100 and a half mirror is employed for the beam splitter 102. In addition, the filter 103 has filter characteristics for the blocking red components contained in the visible light. With this, the visible light passing through the optical path for tracking branched by the beam splitter 102 transmits through the filter 103 and become red-free light. Alternatively, the beam splitter 102 may have optical characteristics for transmitting the infrared light and the red components of the visible light, and reflecting the green components and the blue components of the visible light (i.e., components other than the red components). Incidentally, a light source capable of outputting red-free light may be used. In this case, red-free photography is performed using the CCD image sensor 105 while the red-free light is being irradiated to the eye E. In this case, the filter 103 is not required.

In order to capture a moving image with the light of optimum wavelength bands according to the observation site, for example, the configuration may be employed which is capable of switching the infrared photography and the red-free photography. The control for that purpose may include, for example, switching of the light source, switching of the output wavelengths from the light source, switching of the filter 103, and the like.

The light having transmitted through the filter 103 in this way forms an image by the condenser lens 104 on the light receiving surface of the CCD image sensor 105. The CCD image sensor 105 detects the light having transmitted through the filter 103, for example, at a predetermined frame rate. The CCD image sensor 105 is located in an optical path branched from the signal optical path between the scanner 107 and the deflecting member 100. The intraoperative observation monitor 14 displays an image (observation image) as a live image based on a detection result, obtained by the CCD image sensor 105, of the light having transmitted through the filters 103. The CCD image sensor 105 is an example of the "image sensor" of the embodiment.

The operation controller 106 receives image signals based on the light detected by the CCD image sensor 105 at a time interval corresponding to the frame rate. The operation controller 106 performs arithmetic processing for tracking control based on the image signals (observation image). For example, regarding a plurality of observation images acquired in time series, the operation controller 106 calculates the displacement of the observation images with respect to a predetermined reference observation image. The reference observation image may be, for example, an observation image acquired at a predetermined timing (at the start of observation, at the time when the observation area is set, etc.). The process for calculating the displacement includes, for example, the process of obtaining a displacement between a feature region in the reference observation image and a feature region in another observation image (e.g., in the form of an affine transformation matrix, etc.). Further, the operation controller 106 generates a control signal based on the displacement obtained, and sends the control signal to the scan controller 108. The control signal contains, for example, control content for changing the current scan area by the signal light to a new scan area in which the displacement is canceled. Besides, the operation controller 106 may also be configured to obtain the sum of differences between the reference observation image and the other observation images in a pixel-by-pixel manner, and output a control signal to minimize the sum of the differences to the scan controller 108.

The operation controller 106 may include, for example, field-programmable gate array (FPGA) or a graphics processing unit (GPU), a communication interface, or the like. Further, the operation controller 106 may further include a central processing unit (CPU), a random access memory (RAM), a read only memory (ROM), a hard disk drive, a communication interface, or the like. The storage device such as a hard disk drive stores a computer program for controlling the operation controller 106. The operation controller 106 may include a variety of circuit boards, for example, a circuit board for forming an OCT image.

Based on the control signal from the operation controller 106, the scan controller 108 controls the orientation of at least one of the galvanometer mirror that deflects the signal light in the x direction and the galvanometer mirror that deflects in the y direction, and timing to change the orientation. The scan controller 108 is an example of the "scan controller" of the embodiment. The series of the processes described above are performed repeatedly at a time interval corresponding to the frame rate of the CCD image sensor 105. The time interval may be the same as the frame rate, or may be an integer multiple of the frame rate (that is, a decimation process may be applied here). Thereby, it is possible to follow the scan area by the signal light in real-time with respect to the movement of the eye E.

The signal light passing through the optical path for OCT measurement transmits through the beam splitter 102 and the focus lens 101 together with the aiming light, and is guided to the eye E by the deflecting member 100. Backscattered light of the signal light due to the fundus and the like travels the same path as the forward path in the opposite direction and reaches the OCT unit 150 and the CCD image sensor 105. The aiming light reflected by the fundus and the like transmits through the deflecting member 100, and is incident on the observation optical system 30.

OCT Unit

Figure 5:
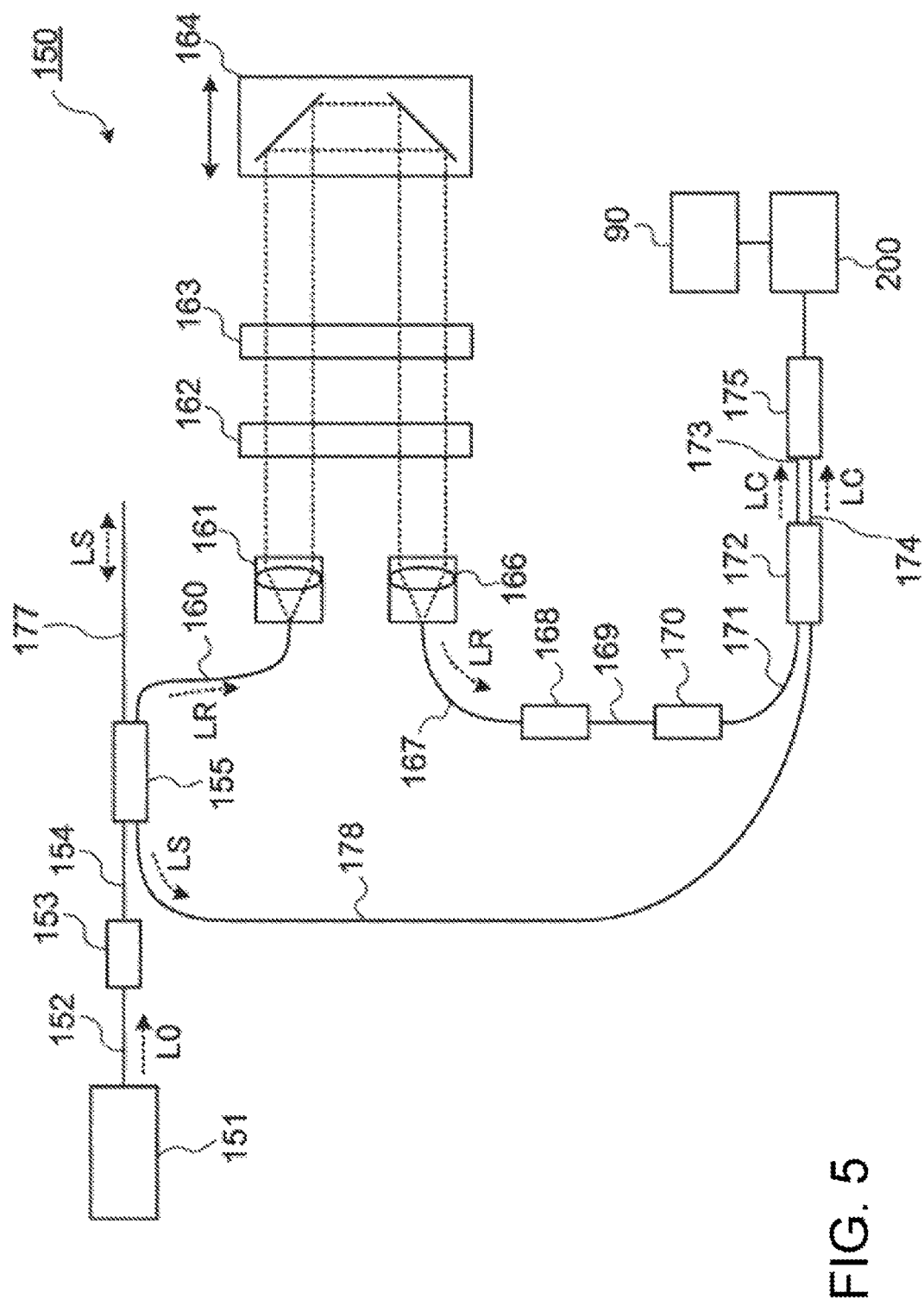
FIG. 5 is a schematic diagram illustrating an example of the configuration of an OCT unit of the ophthalmic surgical apparatus according to the embodiment.

FIG. 5 illustrates an example of the configuration of the OCT unit 150. The OCT unit 150 is provided with an optical system is provided for acquiring an OCT image of the eye E. The optical system may have the same configuration as a conventional swept-source OCT device. Specifically, the optical system is an interference optical system that includes a splitting unit that splits the light output from the wavelength tunable light source (wavelength sweeping light source) into signal light and reference light, and an interference unit that superposes the signal light having passed through the eye with the reference light having passed through the reference optical path to interfere with one another, and the interference optical system detects interference light generated by the interference unit. The interference optical system may further include the scanner 107 configured to scan the eye E undergoing surgery with light guided through the signal optical path. The detection result of the interference light obtained by the interference optical system (detection signal) is a signal indicating the spectra of the interference light, and is sent to the arithmetic and control unit 200.

A light source unit 151, as with a general swept-source OCT device, includes a wavelength tunable light source (wavelength sweeping light source) capable of varying (sweeping) the wavelength of emitted light. The light source unit 151 causes a temporal variation of the output wavelengths in the wavelength bands of near infrared light that cannot be sensed by the human eye. The light output from the light source unit 151 is denoted by L0.

The light L0 output from the light source unit 151 is guided through an optical fiber 152 to a polarization controller 153 and its polarization state is adjusted. For example, the polarization controller 153 adjusts the polarization state of the light L0, which is guided through the optical fiber 152, by applying stress from the outside to the optical fiber 152 in a loop configuration.

The light L0, polarization state of which has been adjusted by the polarization controller 153, is guided through an optical fiber 154 to a fiber coupler 155, and split into reference light LR and signal light LS.

The reference light LR is guided through an optical fiber 160 to a collimator 161, and collimated into a parallel light beam. The reference light LR collimated into a parallel light beam travels through an optical path length correction member 162 and a dispersion compensating member 163, and is guided to a corner cube 164. The optical path length correction member 162 acts as a delaying member for matching the optical path length (optical distance) of the reference light LR with that of the signal light LS. The dispersion compensating member 163 acts as a dispersion compensating member for matching the dispersion characteristics of the reference light LR with that of the signal light LS.

The corner cube 164 reverses the traveling direction of the reference light LR, which has been collimated into a parallel light beam by the collimator 161. The optical path (entrance optical path) of the reference light LR that travels toward the corner cube 164 and the optical path (emission optical path) of the reference light LR that travels from the corner cube 164 are parallel to one another. The corner cube 164 is configured to be movable in the direction along the entrance optical path and the emission optical path of the reference light LR. With this movement, the length of the optical path of the reference light LR (reference optical path) is changed.

The reference light LR having passed through the corner cube 164 travels through the dispersion compensation member 163 and the optical path length correction member 162, and is converted into a converging light beam from a collimated light beam by a collimator 166. The reference light LR then enters an optical fiber 167, and is guided to a polarization controller 168. Thereby, the polarization state of the reference light LR is adjusted.

For example, the polarization controller 168 has a configuration similar to that of the polarization controller 153. The reference light LR, polarization state of which has been adjusted by the polarization controller 168, is guided through an optical fiber 169 to an attenuator 170. The amount of light is adjusted under the control of the arithmetic and control unit 200. The reference light LR, the amount of light of which has been adjusted by the attenuator 170, is guided through an optical fiber 171 to a fiber coupler 172.

The signal light LS generated by the fiber coupler 155 is guided through an optical fiber 177 to the first optical unit 16. The signal light LS having entered the first optical unit 16 travels through the combining unit 109, the scanner 107, the beam splitter 102, and the focus lens 101, and reaches the deflecting member 100. Then, the signal light LS is reflected by the deflecting member 100, and is irradiated to the eye E. The signal light LS is scattered (and reflected) at various depth positions of the eye E. Backscattered light of the signal light LS due to the eye E travels the same path as the forward path in the opposite direction, and is guided to the fiber coupler 155. Thus, the signal light LS reaches the fiber coupler 172 through an optical fiber 178.

The fiber coupler 172 superposes the signal light LS incident via the optical fiber 178 with the reference light LR incident via the optical fiber 171 to couple (interfere) with each other to generate interference light. The fiber coupler 172 splits the interference light of the signal light LS and the reference light LR at a predetermined splitting ratio (e.g., 50:50) to generate a pair of interference light beams LC. The pair of interference light beams LC output from the fiber coupler 172 is respectively guided through optical fibers 173 and 174 to a detector 175.

For example, the detector 175 is a balanced photo diode (BPD) that includes a pair of photodetectors each configured to detect corresponding one of the pair of interference light beams LC, and outputs the difference between their detection results. The detector 175 sends the result of difference (detection signal) to the arithmetic and control unit 200. The arithmetic and control unit 200 forms a tomographic image by, for example, applying a Fourier transform and the like to the spectral distribution based on the detection signals obtained by the detector 175 with respect to each set of wavelength sweeping (that is, with respect to each A-line). The arithmetic and control unit 200 displays the image on the display 90.

Although an interferometer of Michelson type is employed in this embodiment, it is possible to employ any type of interferometer such as an interferometer Mach-Zehnder type as needed. In this embodiment, the interference optical system includes the fiber couplers 155 and 172, the detector 175; and optical fibers and various optical elements for guiding the reference light LR and the signal light LS between them. The interference optical system may further include the light source unit 151. The interference optical system is an example of the "interference optical system" of the embodiment.

Arithmetic and Control Unit

Described below is the configuration of the arithmetic and control unit 200. The arithmetic and control unit 200 analyzes the detection signals fed from the detector 175 to form an OCT image of the eye. An arithmetic process for this is the same as that of a conventional swept-source OCT.

Further, the arithmetic and control unit 200 controls each part of the OCT unit 150. For example, the arithmetic and control unit 200 displays an OCT image of the eye on the display 90. As the control of the OCT unit 150, the arithmetic and control unit 200 controls the operation of the light source unit 151, the movement of the corner cube 164, the operation of the detector 175, the operation of the attenuator 170, the operation of the polarization controllers 153 and 168, and the like.

The arithmetic and control unit 200 includes a microprocessor, RAM, ROM, a hard disk drive, a communication interface, and the like, as in conventional computers. The storage device such as a hard disk drive stores a computer program for controlling the ophthalmic surgical microscope 1. The arithmetic and control unit 200 may be provided with various types of circuit boards, such as a circuit board for forming OCT images. The arithmetic and control unit 200 may further include an operation device (input device) such as a keyboard and a mouse, and a display such as an LCD.

Control System

Figure 6:
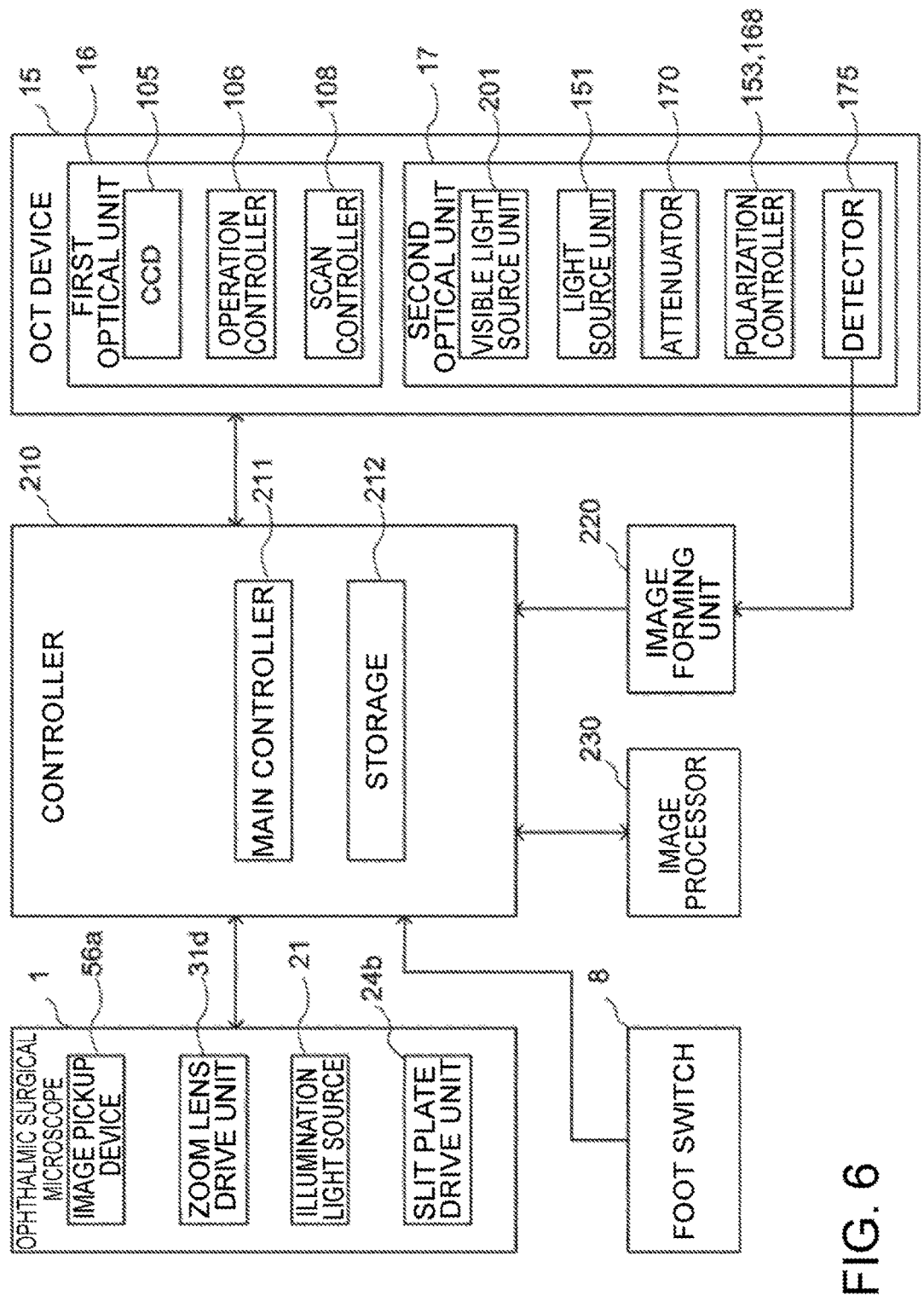
FIG. 6 is a schematic diagram illustrating an example of the configuration of a control system of the ophthalmic surgical apparatus according to the embodiment.

FIG. 6 illustrates an example of the configuration of the control system of the ophthalmic surgical apparatus 40. In FIG. 6, like reference symbols designate like parts as in FIGS. 1 to 5, and the explanation thereof is omitted as appropriate.

Controller

A controller 210 functions as the center of the control system of the ophthalmic surgical apparatus 40. The controller 210 has functions of both a control unit (operation control unit) for controlling the ophthalmic surgical microscope 1, and a control unit (arithmetic and control unit 200) for controlling the OCT device 15. One or more elements for realizing these units may be distributed to the ophthalmic surgical microscope 1 and the OCT device 15. The controller 210 includes, for example, the aforementioned microprocessor, RAM, ROM, a hard disk drive, a communication interface, and the like. The controller 210 is provided with a main controller 211 and a storage 212.

Main Controller

The main controller 211 performs various types of controls mentioned above. In particular, the main controller 211 controls the image pickup device 56a, a zoom lens drive unit 31d, the illumination light source 21, and a slit plate drive unit 24b of the ophthalmic surgical microscope 1. The main controller 211 also controls the CCD image sensor 105, the operation controller 106, and the scan controller 108 of the first optical unit 16. Further, the main controller 211 controls the visible light source unit 201, the light source unit 151, the attenuator 170, the polarization controllers 153 and 168, and the detector 175 of the second optical unit 17.

For example, of the controller 210, a control unit for controlling the components of the ophthalmic surgical microscope 1 (e.g. the image pickup device 56a, the zoom lens drive unit 31d, the illumination light source 21, the slit plate drive unit 24b, etc.) is provided to the ophthalmic surgical microscope 1. Further, of the main controller 211, a control unit for controlling the components of the OCT device 15 (e.g., the CCD image sensor 105, the scan controller 108, the visible light source unit 201, the light source unit 151, the attenuator 170, the polarization controller 153 and 168, the detector 175, etc.) is provided to the OCT device 15 (the first optical unit 16 or the second optical unit 17). That is, the controller 210 includes the operation controller 106, the scan controller 108, and the arithmetic and control unit 200 illustrated in FIG. 4, as well as an arithmetic and control unit of the ophthalmic surgical microscope 1 (not illustrated). In other words, the main controller 211 may include two or more arithmetic and control units distributed to the ophthalmic surgical microscope 1 and the OCT device 15.

In this case, the operation mode of the main controller 211 may be changed based on the result of detection as to whether the first optical unit 16 is attached to the microscope 6 by a known detector. For example, in response to the detection of an event that the first optical unit 16 is attached to the microscope 6, the main controller 211 switches its operation mode to the mode in which two or more arithmetic and control units operate in cooperation. For example, when the OCT device 15 acquires an OCT image, an observation image or the like, the arithmetic and control unit 200 sends a control signal to the control unit of the ophthalmic surgical microscope 1. Having received the control signal, the control unit controls the display operation of the display 90 or the intraoperative observation monitor 14. Besides, in response to the detection of an event that the first optical unit 16 is removed from the microscope 6, the main controller 211 switches its operation mode from the cooperative operation mode to the mode in which the control unit of the ophthalmic surgical microscope 1 operates alone.

The zoom lens drive unit 31d moves the zoom lenses 31a, 31b and 31c, which constitutes the zoom lens system 31, in the direction along the observation optical axes OR and OL independently of one another. The slit plate drive unit 24b moves the slit plate 24 in a direction perpendicular to the illumination optical axis O'.

Further, the main controller 211 performs the process of writing data to and reading data from the storage 212. The main controller 211 displays an image based on the light having transmitted through the filters 103 detected by the CCD image sensor 105 on the intraoperative observation monitor 14.

Image Forming Unit

An image forming unit 220 forms image data of a cross-sectional image of the fundus or the like based on a detection signal from the detector 175. As with a conventional swept-source OCT, this process includes noise removal (noise reduction), filtering, fast Fourier transform (FFT), and the like. In the case of OCT devices of other types, the image forming unit 220 performs a known process corresponding to the type. Of the arithmetic and control unit 200 illustrated in FIG. 4, the image forming unit 220 includes a component for forming an OCT image. The image forming unit 220 may also include a component related to the forming of images in the arithmetic and control unit of the ophthalmic surgical microscope 1.

Image Processor

An image processor 230 performs various types of image processing and analysis on the image formed by the image forming unit 220. For example, the image processor 230 performs various kinds of correction processes such as luminance correction and dispersion compensation of the image. Further, the image processor 230 may perform various types of image processing and analysis on an image (fundus image, anterior eye image, etc.) obtained by the ophthalmic surgical microscope 1. Of the arithmetic and control unit 200 illustrated in FIG. 4, the image processor 230 includes a component for processing an OCT image, a component for processing an image output from the CCD image sensor 105 of the operation controller 106, and a component related to image processing in the arithmetic and control unit of the ophthalmic surgical microscope 1.

The data processor 230 performs known image processing such as an interpolation process for interpolating pixels between cross-sectional images, thereby forming image data of a three-dimensional image of the fundus or the like. The image data of a three-dimensional image refers to image data in which the positions of pixels are defined by a three-dimensional coordinate system Examples of the image data of a three-dimensional image include image data composed of three-dimensional arrays of voxels. This image data is referred to as volume data, voxel data, or the like. For displaying an image based on the volume data, the image processor 230 performs a rendering process (such as volume rendering, maximum intensity projection (MIP), etc.) on the volume data to form image data of a pseudo three-dimensional image taken from a specific view direction. This pseudo three-dimensional image is displayed on a display device such as the display 90.

The image processor 230 may form stack data of a plurality of cross-sectional images as the image data of a three-dimensional image. The stack data is image data obtained by three-dimensionally arranging a plurality of cross-sectional images acquired along a plurality of scanning lines based on the positional relationship of the scanning lines. In other words, the stack data is image data obtained by expressing a plurality of cross-sectional images originally defined by their individual two-dimensional coordinate systems by a single three-dimensional coordinate system (i.e., by embedding the cross-sectional images in a three-dimensional space).

The image processor 230 that functions as described above includes, for example, the aforementioned microprocessor, RAM, ROM, a hard disk drive, a circuit board, and the like. The storage device such as a hard disk drive stores in advance a computer program that causes the microprocessor to implement the above functions.

Incidentally, the ophthalmic surgical apparatus 40 may further include a recording unit configured to record an observation image (visible light) obtained by the observation optical system 30 as a moving image (a storage that stores is as a moving image). For example, the recording unit records image data based on a detection signal obtained by the image pickup device 56a. The recording unit may be a known storage device such as a hard disk drive. The moving image recorded in this way may be read out from the recording unit at an arbitrary timing to be reproduced, and may be displayed on the display 90 or the intraoperative observation monitor 14. The operator can provide instructions to start recording the moving image recorded by the recording unit, stop recording the moving image, reproduce the moving image, and the like by operating the foot switch 8 or an operation panel provided in the intraoperative observation monitor 14 or the display 90, for example. This enables the operator to check surgical procedures for the eye E.

The ophthalmic surgical apparatus 40 may further include a unit configured to record, as a moving image, at least two of an observation image (visible light) obtained by the observation optical system 30, an image captured with the CCD image sensor 105 (an observation image captured by using infrared light, an observation image captured by using red-free light, or the like), and a live image of the OCT image in synchronization with each other. For example, the recording unit records image data based on a detection signal obtained by the image pickup device 56a, image data based on a detection signal obtained by the CCD image sensor 105, and image data formed by the image forming unit 220 or image data subjected to image processing by the image processor 230, and the like. When reproducing the image data thus recorded, the ophthalmic surgical apparatus 40 may synchronize the observation image (visible light) acquired by the observation optical system 30, the infrared observation image captured by infrared photography using the CCD image sensor 105, and the live image of the tree-dimensional OCT image, and display these images in parallel on the display 90 or the intraoperative observation monitor 14. The ophthalmic surgical apparatus 40 may analyze the image in which the aiming light is represented to display the positional relationship between the OCT image and the observation image captured by using the CCD image sensor 105, as a graphic representation, on the observation image. Alternatively, the ophthalmic surgical apparatus 40 may analyze the image in which the aiming light is represented to display the positional relationship between the three-dimensional OCT image and the observation image captured by using the CCD image sensor 105, as a graphic representation, on the observation image. Besides, the operator can provide instructions to start recording the moving image recorded by the recording unit, stop recording the moving image, reproduce the moving image, and the like by operating the foot switch 8 or the operation panel provided in the intraoperative observation monitor 14 or the display 90.

Operation

Described below is the operation of the ophthalmic surgical apparatus 40 having the configuration as described above.

First, the ophthalmic surgical microscope 1 adjusts the conditions of observation. For this purpose, for example, the operator adjusts the ophthalmic surgical microscope 1. More specifically, after adjusting the position and orientation of the second arm 4, the operator moves the microscope 6 in the vertical and horizontal directions by operating the foot switch 8 to place the microscope 6 in a desired position. Then, the operator adjusts the eye width, viewing angle, light intensity, and the like, and matches the focus and the position. With this, the eye E is illuminated with the illumination light of the illumination optical system 20. Thus, the operator can observe the eye E while looking through the eyepiece 37.

After that, the OCT device 15 starts capturing observation images (moving image). Specifically, the OCT device 15 starts acquiring a moving image by infrared photography or red-free photography of the eye E (a site undergoing surgery and around it) from detection signals obtained by the CCD image sensor 105. The images of frames constituting the moving image are temporarily stored in a frame memory (the storage 212), and are sequentially sent to the image processor 230. Further, the image of each frame temporarily stored in the frame memory is displayed on the intraoperative observation monitor 14.

While watching the moving image displayed on the intraoperative observation monitor 14 or a naked eye observation image obtained by the ophthalmic surgical microscope 1, the operator performs focus adjustment by moving the focus lens 101. The main controller 211 may analyze each frame in a known manner to calculate the amount of the movement of the focus lens 101, and perform control to move the focus lens 101 based on the amount of the movement calculated.

Subsequently, the controller 210 starts tracking. Specifically, the operation controller 106 performs arithmetic processing for tracking control based on observation images acquired by the CCD image sensor 105. The scan controller 108 controls the scanner 107 based on a control signal from the operation controller 106. Thereby, it is possible to maintain a suitable positional relationship with the subject in focus at the desired location.

Thereafter, the scan pattern and the scan area by the signal light for OCT measurement (the scan shape and the size of the scan region) are set. The setting of the scan area by the signal light can be performed automatically or manually. In the case of automatic setting of the scan area by the signal light, for example, the same range as in preoperative OCT measurement is reproduced to be set, or the frames of the current observation image are analyzed to detect the site undergoing surgery, and the area including the site undergoing surgery thus detected may be set. The area of the preoperative OCT measurement can be specified by recording the scan area of the OCT measurement performed before the operation in a three-dimensional image or a front image, and by comparing it with the frames of the current observation image. In the case of manual setting of the scan area by the signal light, for example, the operator can set a desired scan area while viewing the live image of an OCT image, the observation image in which the projection image of aiming light is rendered. Incidentally, if the scan area by the signal light is set automatically, the scan area may be identifiably displayed by the projection of aiming light. Besides, examples of the methods of setting the scan pattern include the automatic setting of the same scan pattern as before operation and manual setting using the foot switch 8. When the scan pattern is set manually, options of the scan pattern are displayed on the intraoperative observation monitor 14 or the like, and a desired option is selected using the foot switch 8 or the like. The options of the scan pattern may include at least one of a one-dimensional pattern(s) and a two-dimensional pattern(s).

After completion of the settings for scanning the signal light, OCT measurement is started (note that if a live image of the OCT image is used for the settings, OCT measurement has already been started). The aiming light can be projected in parallel with the implementation of the OCT measurement. In this case, the aiming light is combined with the signal light by the combining unit 109, and is irradiated to the same position as where the signal light is irradiated in the eye E. The aiming light reflected from the eye E enters the observation optical system 30. Thus, the operator can observe the trajectory of the aiming light in the eye E. That is, the operator can visually recognize the scan trajectory of the signal light (the positions where the OCT measurement is being performed).

Further, in order to perform the OCT measurement, as well as controlling the light source unit 151 and the corner cube 164, the controller 210 controls the scanner 107 based on the scan area set as described above. The image forming unit 220 forms a tomographic image of the eye E based on the spectra of the interference light obtained by the OCT measurement. If the scan pattern is three-dimensional scan, the image processor 230 forms a three-dimensional image of the eye E based on a plurality of tomographic images formed by the image forming unit 220.

The controller 210 may display, on the display 90, a still image captured from a moving image displayed on the intraoperative observation monitor 14 in response to operator's operation on the foot switch 8.

The operator performs surgery while selectively performing the observation of the eye E with his/her naked eyes through the ophthalmic surgical microscope 1, the observation of a visible image acquired by the ophthalmic surgical microscope 1, the observation of an OCT image acquired by the OCT device 15, or the observation of an infrared image (or a red-free image) obtained by the OCT device 15.

Effects

Described below are the effects of the ophthalmic surgical apparatus 40 of the embodiment.

According to the embodiment, the ophthalmic surgical apparatus 40 includes the observation optical system 30, the illumination optical system 20, the interference optical system, and the image forming unit 220. The observation optical system 20 is an optical system configured for observing the eye E undergoing surgery through the objective lens 19. The illumination optical system 20 is an optical system configured for illuminating the eye E through the objective lens 19. The interference optical system has a reference optical path and a signal optical path which leads to the eye E through the deflecting member 100 placed between the objective lens 19 and the eye E, and is configured to detect interference light based on light having passed through the signal optical path and returning from the eye E and the reference light having passed through the reference optical path. The image forming unit 220 forms an image of the eye E based on a detection result obtained by the interference optical system.

In the ophthalmic surgical apparatus 40 thus configured, the deflecting member 100 is located between the objective lens 19 and the eye E such that the signal light guided through the signal optical path and the return light thereof are deflected by the deflecting members 100. This prevents the attenuation of the observation light caused by the deflecting member 100 placed for acquiring an OCT image. Thus, high quality observation images and OCT images of the eye E can be acquired during surgery without affecting the existing configuration.

The deflecting member 100 may be located at a position out of at least one of an optical path formed by the observation optical system 30 and an optical path formed by the illumination optical system 20. Alternatively, the deflecting member 100 may be a beam splitter located in at least one of the optical path formed by the observation optical system 30 and the optical path formed by the illumination optical system 20. In addition, the beam splitter may be a dichroic mirror located in the optical path formed by the observation optical system 30. Alternatively, the beam splitter may be a dichroic mirror or a half mirror located in the optical path formed by the illumination optical system 20.

The first optical unit 16, which houses at least part of the interference optical system, may be formed as a detachable attachment for the microscopes 6 that holds at least the objective lens 19. Thus, high quality observation images and OCT images of the eye E can be acquired during surgery without affecting the existing configuration of the ophthalmic surgical microscope 1.

The interference optical system may include the splitting unit, the scanner 107, and the interference unit. The splitting unit splits light from a light source into signal light and reference light. The scanner 107 is used to scan the eye E with light guided through the signal optical path. The interference unit causes the signal light having passed through the signal optical path and returning from the eye E to interfere with the reference light having passed through the reference optical path. In this case, the deflecting member 100 is located between the scanner 107 and the eye E. The first optical unit 16 houses at least the scanner 107 and the deflecting member 100. This results in reduced weight of the first optical unit 16.

The ophthalmic surgical apparatus 40 may further include the combining unit 109. The combining unit 109 combines the signal optical path with an optical path of the visible light from the visible light source unit 201 at a position between the splitting unit and the scanner 107. With this configuration, the operator can check the scan position of OCT measurement while observing the eye E with the observation optical system 30. Thereby, the operator can specify the scan position for capturing an OCT image without taking his/her eye off the eyepiece of the ophthalmic surgical microscope 1. Thus, the efficiency of surgery can be improved.

The first optical unit 16 may further house the CCD image sensor 105. The CCD image sensor 105 is located in an optical path branched from the signal optical path at a position between the scanner 107 and the deflecting member 100. The ophthalmic surgical apparatus 40 may further include the scan controller 108 configured to control the scanner 107 based on an image acquired by the CCD image sensor 105. The first optical unit 16 may further house the scan controller 108. This enables tracking based on signals detected by the CCD image sensor 105.

Besides, at least part of the interference unit and the splitting unit may be housed in the second optical unit 17, and the first optical unit 16 and the second optical unit 17 may be connected by an optical fiber (light guide).

The ophthalmic surgical apparatus 40 may further include the main controller 211 configured to control the observation optical system 30 and the illumination optical system 20. In addition, the main controller 211 may control the interference optical system when the first optical unit 16 is attached to the microscope 6.

The first optical unit 16 (attachment for ophthalmic surgery) is configured to be detachably attached to the ophthalmic surgical microscope 1. The ophthalmic surgical microscope 1 includes the observation optical system 30 configured for observing the eye E undergoing surgery through the objective lens 19, and the illumination optical system 20 configured for illuminating the eye E through the objective lens 19. The first optical unit 16 includes the deflecting member 100, which is located between the objective lens 19 and the eye E in a state of being attached to the ophthalmic surgical microscope 1. In addition, the first optical unit 16 is configured to lead the signal optical path from the interference optical system to the eye E through the deflecting member 100. Here, the interference optical system has the signal optical path and the reference optical path, and is configured to detect interference light based on light having passed through the signal optical path and returning from the eye E and reference light having passed through the reference optical path.

Second Embodiment

While the deflecting member 100 of the first embodiment is described as having rectangular surfaces as illustrated in FIGS. 2 and 3, it is not limited thereto. According to the second embodiment, a deflecting member has a shape corresponding to the optical path formed by the observation optical system 30. In the following, the reference symbols used in the first embodiment are used.

The ophthalmic surgical apparatus of the second embodiment has basically the same configuration and operates in a similar manner as that of the first embodiment. The configuration of the ophthalmic surgical apparatus of the second embodiment differs from that of the ophthalmic surgical apparatus 40 of the first embodiment in the shape of the deflecting member.

Figure 7:
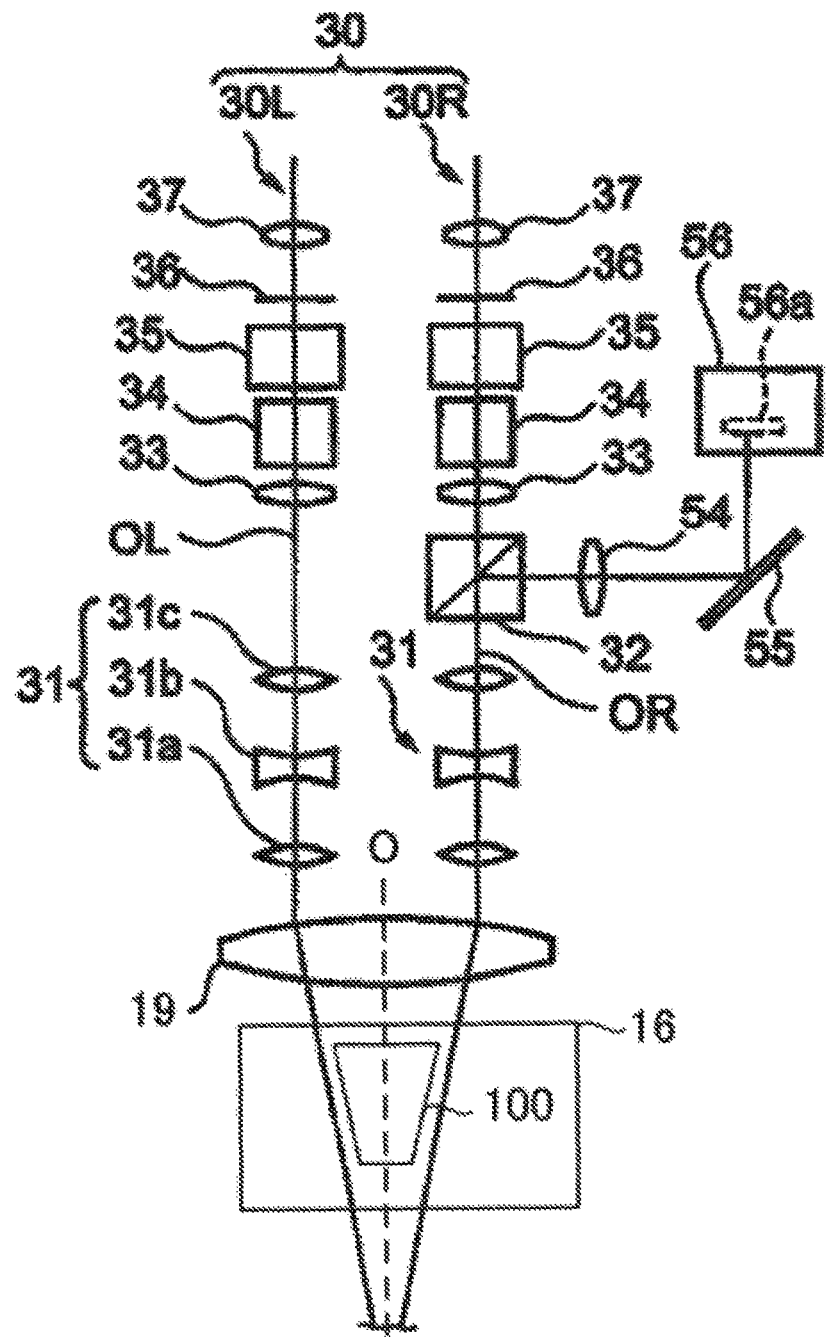
FIG. 7 is a schematic diagram illustrating an example of the configuration of an optical system of an ophthalmic surgical apparatus according to another embodiment.

FIG. 7 illustrates an optical system of the ophthalmic surgical microscope 1 of the second embodiment as viewed from the operator. In FIG. 7, like reference symbols designate like parts as in FIG. 3, and the explanation thereof is omitted as appropriate.

The deflecting member 100 has a bilaterally symmetrical trapezoidal shape as viewed from the front (operator side). Specifically, the deflecting member 100 is formed to have the legs of the trapezoid to be out of the observation optical path. That is, between the objective lens 19 and the eye E, right and left observation optical paths are inclined to get close to each other as they extend toward the eye E. The right and left side surfaces of the deflecting member 100 have a slope corresponding to the right and left observation optical paths, respectively. In other words, the deflecting member 100 is formed such that the area of the lower surface (the surface on the eye E side) is smaller than that of the upper surface (the surface on the objective lens 19 side), and the difference (or ratio) in their areas are set based on, for example, the slopes of the right and left observation optical paths, and the height of the deflecting member 100 (the distance between the upper and lower surfaces). Thus, as in the first embodiment, the attenuation of the observation light can be prevented. Incidentally, the shape of the deflecting member of the embodiment is not limited to that illustrated in FIG. 7. For example, the upper and lower surfaces may be non-parallel, or any of the surfaces may be a curved surface. It is only required that the deflecting member is formed so as not to block the right and left observation optical paths (or so as to block the right and/or left observation optical paths at a level that does not cause a substantial influence on observation), and the polarization member is located below the objective lens 19.

The ophthalmic surgical apparatus of this embodiment can achieve the same effect as the first embodiment.

Third Embodiment

In the first embodiment and the second embodiment, the deflecting member is described as being located between the objective lens 19 and the eye E undergoing surgery; however, this is not so limited. In the following, the reference symbols used in the first embodiment are used.

The ophthalmic surgical apparatus of the third embodiment has basically the same configuration and operates in a similar manner as that of the first embodiment. The configuration of the ophthalmic surgical apparatus of the third embodiment differs from that of the ophthalmic surgical apparatus 40 of the first embodiment in a position where the deflecting member is located.

Figure 8:
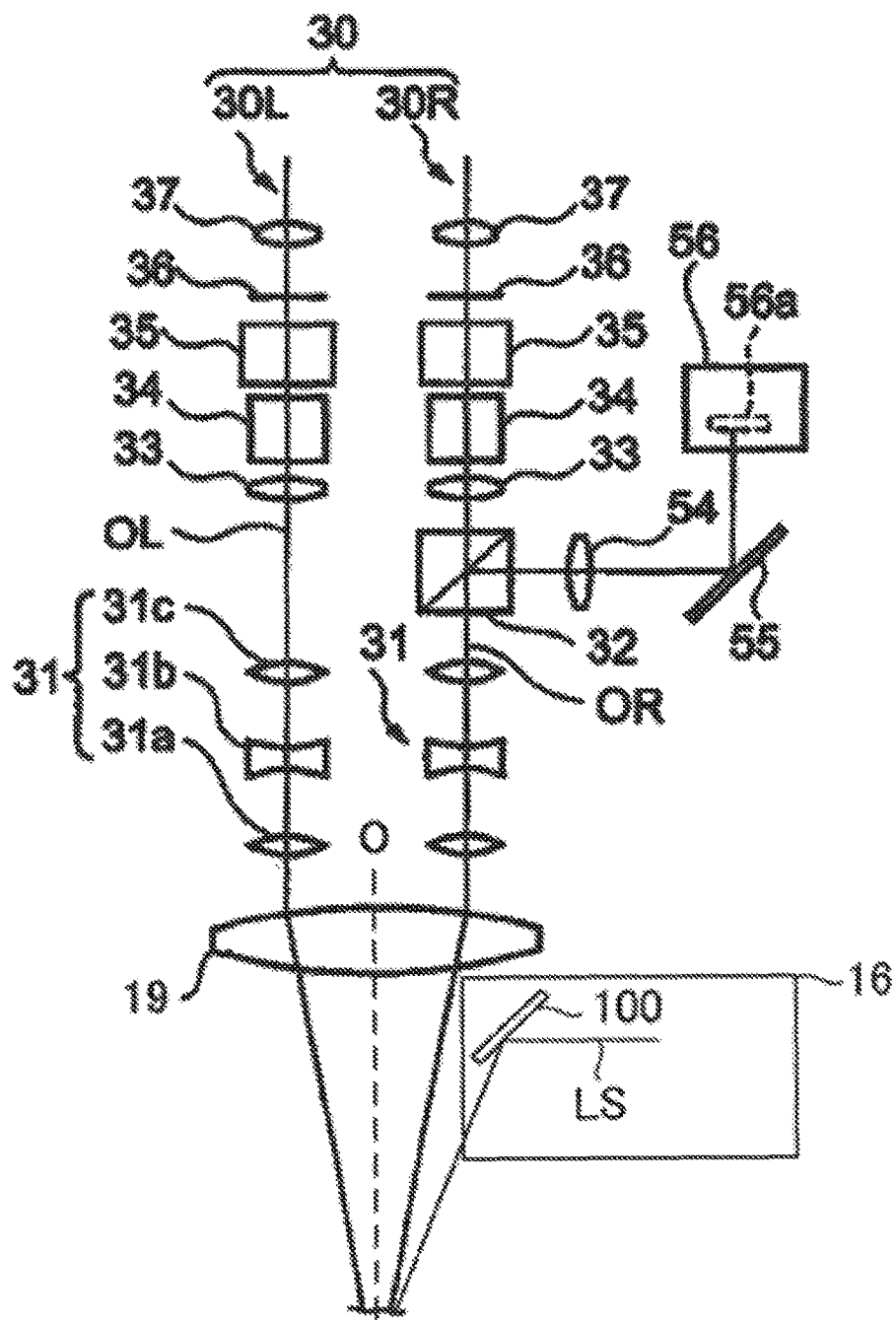
FIG. 8 is a schematic diagram illustrating an example of the configuration of an optical system of an ophthalmic surgical apparatus according to another embodiment.

FIG. 8 illustrates an optical system of the ophthalmic surgical microscope 1 of the third embodiment as viewed from the operator. In FIG. 8, like reference symbols designate like parts as in FIG. 3, and the explanation thereof is omitted as appropriate.

In the third embodiment, the deflecting member 100 is located in a predetermined position in a direction perpendicular to the optical axis O of the objective lens 19 between the objective lens 19 and the eye E so as to be out of the optical path formed by the observation optical system 30. Thus, as in the first embodiment, the attenuation of the observation light can be prevented. Incidentally, the incident angle of the signal light with respect to the eye E can be closer to 90 degrees as the predetermined position is closer to the optical axis O. This improves the detection accuracy of the return light of the signal light. Thereby, the quality of the OCT image can be improved. In contrast, if the predetermined position is close to the optical axis O, it becomes closer to the optical path formed by the observation optical system 30. As a result, the implementation may become difficult. The distance between the optical axis O and the predetermined position can be appropriately designed in consideration of the above.

The ophthalmic surgical apparatus of this embodiment can achieve the same effect as the first embodiment.

Fourth Embodiment

In the first to third embodiments, the deflecting member is described as being located between the objective lens 19 and the eye E undergoing surgery; however, this is not so limited. In the following, the reference symbols used in the first embodiment are used.

The ophthalmic surgical apparatus of the fourth embodiment has basically the same configuration and operates in a similar manner as that of the first embodiment. The configuration of the ophthalmic surgical apparatus of the fourth embodiment differs from that of the ophthalmic surgical apparatus 40 of the first embodiment in a position where the deflecting member is located.

Figure 9:
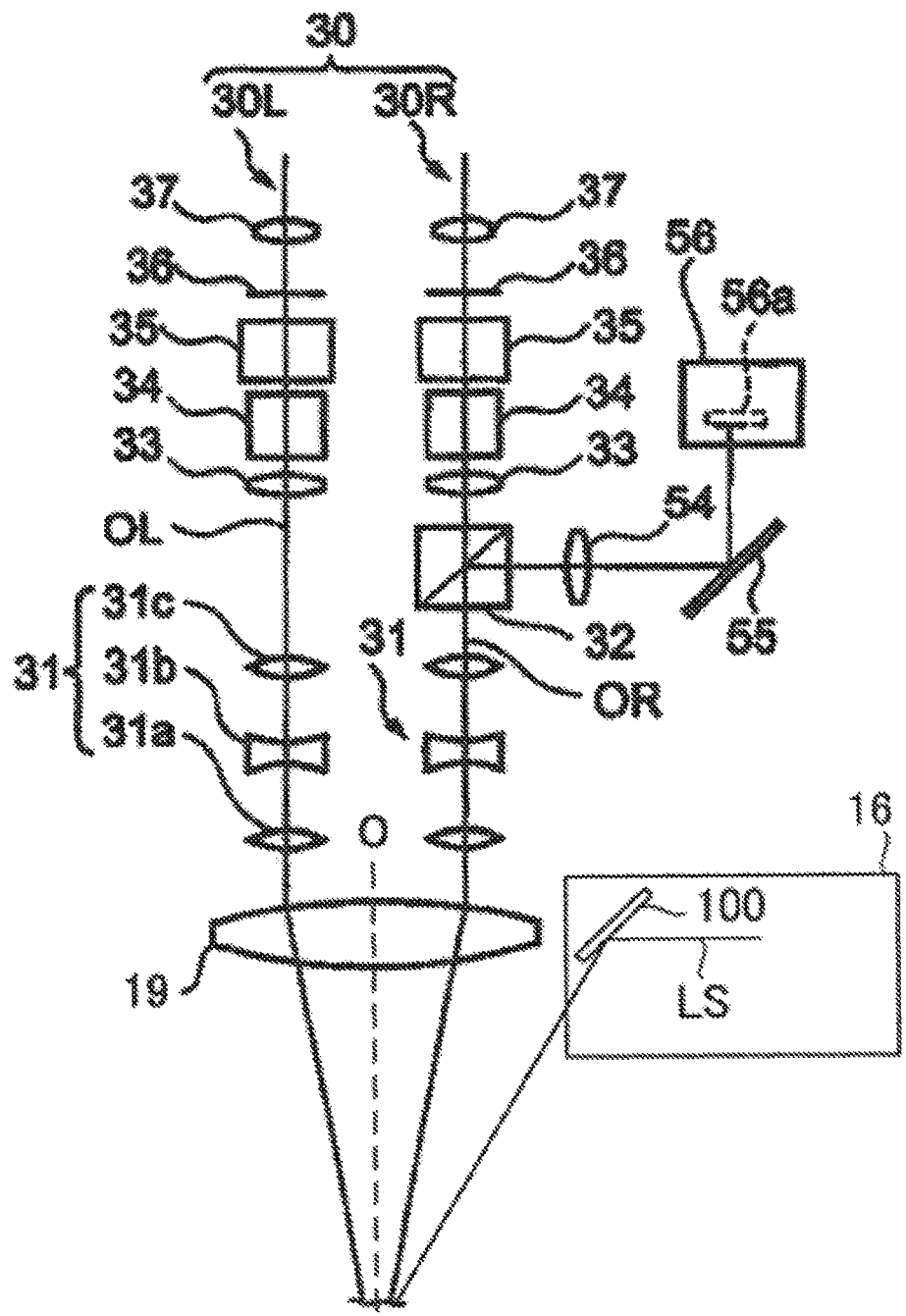
FIG. 9 is a schematic diagram illustrating an example of the configuration of an optical system of an ophthalmic surgical apparatus according to another embodiment.

FIG. 9 illustrates an optical system of the ophthalmic surgical microscope 1 of the fourth embodiment as viewed from the operator. In FIG. 9, like reference symbols designate like parts as in FIG. 3, and the explanation thereof is omitted as appropriate.

In the fourth embodiment, the deflecting member 100 is located in a predetermined position in a direction perpendicular to the optical axis O of the objective lens 19 from the periphery of the objective lens 19 so as to be out of the optical path formed by the observation optical system 30.

Thus, in addition to the effects achieved in the first embodiment, the attenuation of the illumination light can be prevented. Incidentally, the incident angle of the signal light with respect to the eye E can be closer to 90 degrees as the predetermined position is closer to the optical axis O. This improves the detection accuracy of the return light of the signal light. Thereby, the quality of the OCT image can be improved. In contrast, if the predetermined position is close to the optical axis O, the deflecting member 100 may physically interfere with the objective lens 19. The distance between the optical axis O and the predetermined position can be appropriately designed in consideration of the above.

Effects

Described below are the effects of the ophthalmic surgical apparatus of this embodiment.

According to the embodiment, the ophthalmic surgical apparatus includes the observation optical system 30, the illumination optical system 20, the interference optical system, and the image forming unit 220. The observation optical system is an optical system configured for observing the eye E undergoing surgery through the objective lens 19. The illumination optical system 20 is an optical system configured for illuminating the eye E through the objective lens 19. The interference optical system has a reference optical path and a signal optical path which leads to the eye E through the deflecting member 100 placed in a predetermined position in a direction perpendicular to the optical axis O of the objective lens 19 from the periphery of the objective lens 19, and is configured to detect interference light based on light having passed through the signal optical path and returning from the eye E and the reference light having passed through the reference optical path. The image forming unit 220 forms an image of the eye E based on a detection result obtained by the interference optical system.

In the ophthalmic surgical apparatus thus configured, the deflecting member 100 is located in a predetermined position in a direction perpendicular to the optical axis O of the objective lens 19 from the periphery of the objective lens 19 such that the signal light guided through the signal optical path and the return light thereof are deflected by the deflecting members 100. This prevents the attenuation of both the observation light and the illumination light caused by the deflecting member placed for acquiring an OCT image. Thus, high quality observation images and OCT images of the eye E can be acquired during surgery without affecting the existing configuration.

The first optical unit 16 (attachment for ophthalmic surgery) is configured to be detachably attached to the ophthalmic surgical microscope 1. The ophthalmic surgical microscope 1 includes the observation optical system 30 configured for observing the eye E undergoing surgery through the objective lens 19, and the illumination optical system 20 configured for illuminating the eye E through the objective lens 19. The first optical unit 16 includes the deflecting member 100, which is located in a predetermined position in a direction perpendicular to the optical axis O of the objective lens 19 from the periphery of the objective lens 19 in a state of being attached to the ophthalmic surgical microscope 1. In addition, the first optical unit 16 is configured to lead the signal optical path from the interference optical system to the eye E through the deflecting member 100. Here, the interference optical system has the signal optical path and the reference optical path, and is configured to detect interference light based on light having passed through the signal optical path and returning from the eye E and reference light having passed through the reference optical path.

Fifth Embodiment

In the first to fourth embodiments, the deflecting member 100 is described as being located at a predetermined distance from the objective lens 19 in the downward or horizontal direction; however, this is not so limited. In the fifth embodiment, the deflecting member 100 is above the objective lens 19. In the following, the reference symbols used in the first embodiment are used.

The ophthalmic surgical apparatus of the fifth embodiment has basically the same configuration and operates in a similar manner as that of the first embodiment. The configuration of the ophthalmic surgical apparatus of the fifth embodiment differs from that of the ophthalmic surgical apparatus 40 of the first embodiment in positions where the objective lens and the deflecting member are located.

Figure 10:
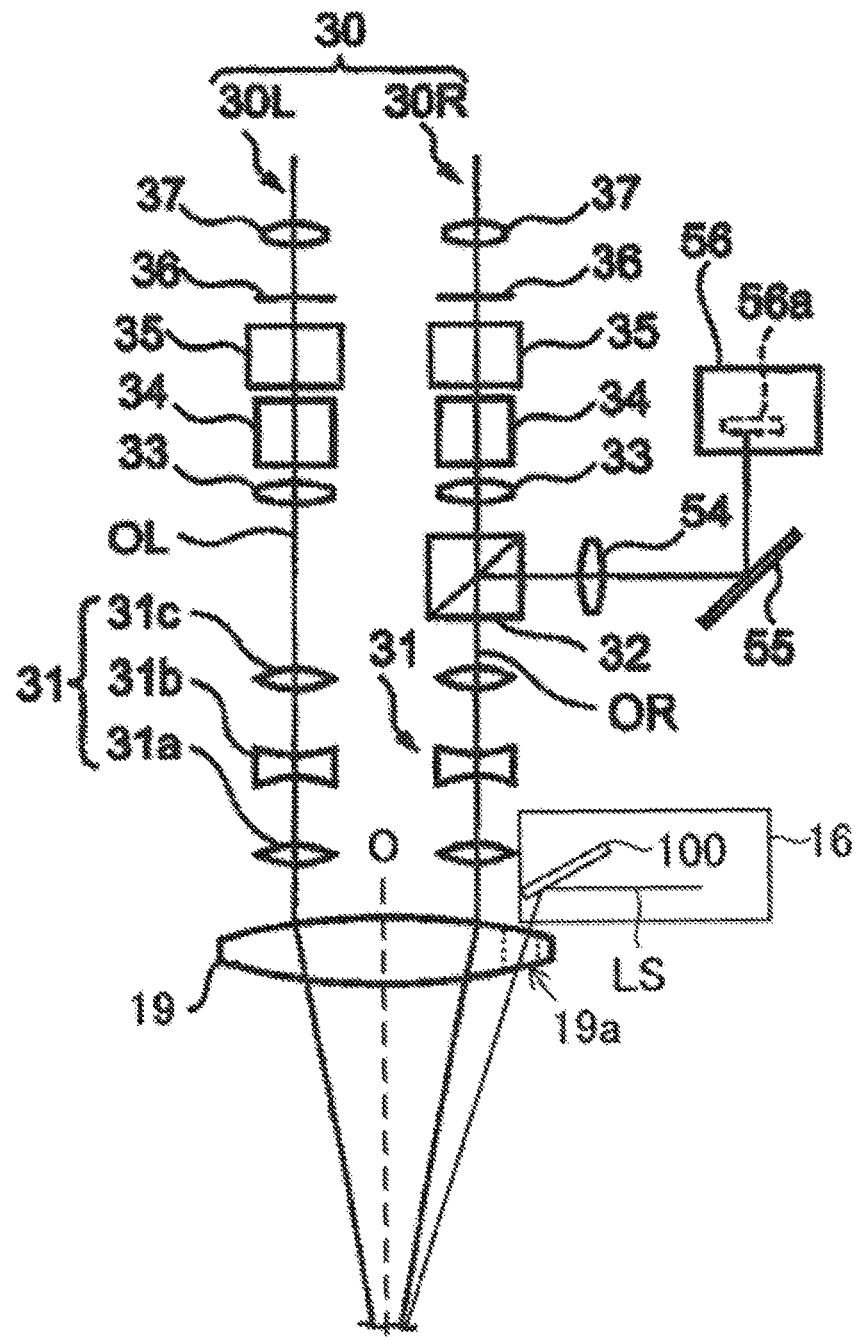
FIG. 10 is a schematic diagram illustrating an example of the configuration of an optical system of an ophthalmic surgical apparatus according to another embodiment.

FIG. 10 illustrates an optical system of the ophthalmic surgical microscope 1 of the fifth embodiment as viewed from the operator. In FIG. 10, like reference symbols designate like parts as in FIG. 3, and the explanation thereof is omitted as appropriate.

In the fifth embodiment, the deflecting member 100 is located between the objective lens 19 and the zoom lens system 31 so as to be out of the optical path formed by the observation optical system 30. In the objective lens 19, a part where the signal optical path passes through and a part where the optical path formed by the observation optical system passes through have different refractive properties. In this embodiment, a hole 19a is formed in the objective lens 19. The deflecting member 100 is located such that the part where the signal optical path passes through passes through the hole 19a. Thus, in addition to the effects achieved in the first embodiment, the attenuation of the illumination light can be prevented.

Effects

Described below are the effects of the ophthalmic surgical apparatus of this embodiment.

According to the embodiment, the ophthalmic surgical apparatus includes the observation optical system 30, the illumination optical system 20, the interference optical system, and the image forming unit 220. The observation optical system 30 includes the zoom lens system 31, and is an optical system configured for observing the eye E undergoing surgery through the objective lens 19. The illumination optical system 20 is an optical system configured for illuminating the eye E through the objective lens 19. The interference optical system has a reference optical path and a signal optical path which leads to the eye E through the deflecting member 100 placed between the objective lens 19 and the zoom lens system 31, and is configured to detect interference light based on light having passed through the signal optical path and returning from the eye E and the reference light having passed through the reference optical path. The image forming unit 220 forms an image of the eye E based on a detection result obtained by the interference optical system. In the objective lens 19, the part where the signal optical path passes through and the part where the optical path formed by the observation optical system 30 passes through have different refractive properties.

In the ophthalmic surgical apparatus 40 thus configured, the deflecting member 100 is located between the objective lens 19 and the zoom lens system 31. In addition, in the objective lens 19, the part where the signal optical path passes through and the part where the optical path formed by the observation optical system 30 passes through have different refractive properties. Such a configuration prevents the attenuation of the observation light and the illumination light caused by the deflecting member placed for acquiring an OCT image. Thus, high quality observation images and OCT images of the eye E can be acquired during surgery without affecting the existing configuration. Further, if the part of the objective lens 19, where the signal optical path passes through, has refractive properties in consideration of the incident angle of the signal light with respect to the objective lens 19 or the eye E, scattering of the signal light and the return light thereof can be prevented. As a result, higher quality OCT images can be acquired.

The first optical unit 16 (attachment for ophthalmic surgery) is configured to be detachably attached to the ophthalmic surgical microscope 1. The ophthalmic surgical microscope 1 includes the observation optical system 30 that includes the zoom lens system 31, and configured for observing the eye E undergoing surgery through the objective lens 19, and the illumination optical system 20 configured for illuminating the eye E through the objective lens 19. In addition, in the objective lens 19, the part where the signal optical path passes through and the part where the optical path formed by the observation optical system 30 passes through have different refractive properties. The first optical unit 16 includes the deflecting member 100, which is located between the objective lens 19 and the zoom lens system 31 in a state of being attached to the ophthalmic surgical microscope 1. In addition, the first optical unit 16 is configured to lead the signal optical path from the interference optical system. Here, the interference optical system has the signal optical path and the reference optical path, and is configured to detect interference light based on light having passed through the signal optical path and returning from the eye E and reference light having passed through the reference optical path.

Sixth Embodiment

In the first to fifth embodiments, the deflecting member is described as being located around the objective lens 19; however, this is not so limited. In the following, the reference symbols used in the first embodiment are used.

The ophthalmic surgical apparatus of the sixth embodiment has basically the same configuration and operates in a similar manner as that of the first embodiment. The configuration of the ophthalmic surgical apparatus of the sixth embodiment differs from that of the ophthalmic surgical apparatus 40 of the first embodiment in the objective lens.

Figure 11:
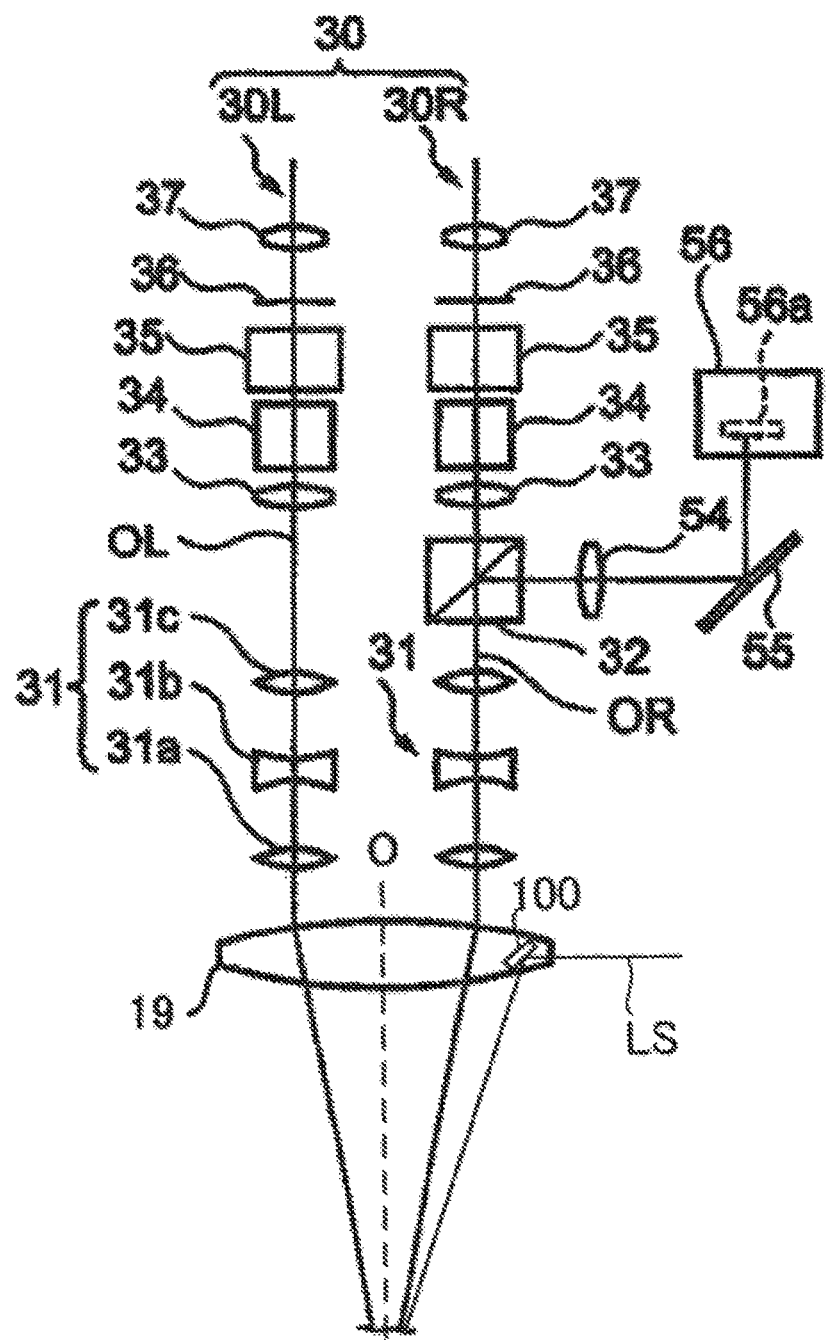
FIG. 11 is a schematic diagram illustrating an example of the configuration of an optical system of an ophthalmic surgical apparatus according to another embodiment.

FIG. 11 illustrates an optical system of the ophthalmic surgical microscope 1 of the sixth embodiment as viewed from the operator. In FIG. 11, like reference symbols designate like parts as in FIG. 3, and the explanation thereof is omitted as appropriate.

In the sixth embodiment, the objective lens 19 is provided with the deflecting member 100. Although FIG. 11 illustrates the case where the deflecting member 100 is located inside the objective lens 19, the deflecting member 100 may be located on the front surface (e.g., the surface on the eye E side) or the back surface (e.g., the surface on the zoom lens system 31 side) of the objective lens 19. In this embodiment, the signal light passing through the signal optical path is deflected by the deflecting member 100 located inside the objective lens 19. For example, the signal light is incident on the objective lens 19 from the normal direction of the cross section in the vertical direction which is formed on the objective lens 19, and is deflected by the deflecting member 100 arranged inside the objective lens 19. Thus, in addition to the effects achieved in the first embodiment, the attenuation of the illumination light can be prevented.

Effects

Described below are the effects of the ophthalmic surgical apparatus of this embodiment.

According to the embodiment, the ophthalmic surgical apparatus includes the observation optical system 30, the illumination optical system 20, the interference optical system, and the image forming unit 220. The observation optical system is an optical system configured for observing the eye E undergoing surgery through the objective lens 19 which is provided with the deflecting member 100. The illumination optical system 20 is an optical system configured for illuminating the eye E through the objective lens 19. The interference optical system has a reference optical path and a signal optical path which leads to the eye E through the deflecting member 100 located in the objective lens 19, and is configured to detect interference light based on light having passed through the signal optical path and returning from the eye E and the reference light having passed through the reference optical path. The image forming unit 220 forms an image of the eye E based on a detection result obtained by the interference optical system.

In the ophthalmic surgical apparatus 40 thus configured, the deflecting member 100 is located in the objective lens 19 so as to deflect the signal light guided through the signal optical path and the return light thereof by the deflecting member 100 located in the objective lens 19. This prevents the attenuation of both the observation light and the illumination light caused by the deflecting member placed for acquiring an OCT image. Thus, high quality observation images and OCT images of the eye E can be acquired during surgery without affecting the existing configuration.

MODIFICATIONS

The embodiments described above are mere examples for embodying or carrying out the present invention, and therefore susceptible to several modifications and variations (omission, substitution, addition, etc.), all coming within the scope of the invention.

First Modification

In the embodiments described above, the connecting portion (connector, port) where the first optical unit 16 formed as an attachment is attached to the microscope 6 (main body) may be configured to be connectable to an attachment other than the first optical unit 16. That is, the microscope 6 is provided with a first connecting portion. The first optical unit 16 is provided with a second connecting portion. When the first connection portion and the second connecting portion are connected to each other, the first optical unit 16 is attached to the microscope 6. The first connecting portion is configured to be connectable to a third connecting portion of an attachment other than the first optical unit 16.

Thereby, the first connecting portion of the microscope 6 can be used widely. Thus, it is possible to dispense with an additional connecting portion for another attachment.

Second Modification

In the embodiments described above, an optical unit (fourth optical unit) that houses at least part of the interference optical system may be attached to an optical unit (third optical unit) that houses at least the deflecting member 100. The other optical unit (fourth optical unit) that houses at least part of the interference optical system is configured to be detachably attached to the optical unit (third optical unit), which is being attached to the microscope 6 (main body) that has at least the objective lens 19.

Third Modification

In the embodiments described above, the ophthalmic surgical apparatus may further include a mechanism configured for moving the deflecting member 100. With this, the deflecting member 100 can be moved to a predetermined position only on the occasion of acquiring an OCT image. Thereby, it is possible to acquire high-quality observation images of the eye E when acquisition of an OCT image is not required. Moreover, in the case where the mechanism is provided to the attachment for ophthalmic surgery, and if the attachment is configured to be attachable to various ophthalmic surgical microscopes, the position of the deflecting member 100 can be adjusted according to the arrangement of the optical path of the ophthalmic surgical microscope to which the attachment is being attached.

Other Modifications

In the embodiments described above, the first optical unit 16 may be attached between the attachment portion of the front lens 13 and the front lens 13.

In the embodiments described above, the deflecting member 100 may include an optical element having at least a function to change the traveling direction of light, such as a plane mirror, a non-planar mirror such as a concave mirror, a deflecting prism or a diffraction grating.

While, in the embodiments described above, the OCT device 15 is described as including the first optical unit 16 and the second optical unit 17, it may include three or more optical units.

The connecting portion (second connecting portion) of the attachment for ophthalmic surgery can be configured to be interchangeable. That is, two or more second connecting portions are prepared such that the second connecting portions can be selectively used according to the form of the connecting portion (first connecting portion) of the ophthalmic surgical microscope to which the attachment is to be attached. Thereby, the same attachment for ophthalmic surgery can be attached to various types of ophthalmic surgical microscopes each having the first connecting portion in a different form.

Further, the configurations described in the first to sixth embodiments and the above modifications can be combined arbitrarily. For example, in a system to which two or more of the first to sixth embodiments can be applied, a desired one of the two or more embodiments can be alternatively applied by switching the operation mode.

ASPECTS OF EMBODIMENTS

Exemplary aspects of embodiments are described below.
(Aspect 1)
An ophthalmic surgical apparatus comprising:
an observation optical system configured to observe an eye undergoing surgery through an objective lens;
an illumination optical system configured to illuminate the eye through the objective lens;
an interference optical system having a reference optical path and a signal optical path which leads to the eye through a deflecting member located between the objective lens and the eye, and configured to detect interference light based on light having passed through the signal optical path and returning from the eye, and reference light having passed through the reference optical path; and
an image forming unit configured to form an image of the eye based on a detection result obtained by the interference optical system.
(Aspect 2)
An ophthalmic surgical apparatus comprising:
an observation optical system configured to observe an eye undergoing surgery through an objective lens;
an illumination optical system configured to illuminate the eye through the objective lens;
an interference optical system having a reference optical path and a signal optical path which leads to the eye through a deflecting member located in a predetermined position in a direction perpendicular to an optical axis of the objective lens from periphery of the objective lens, and configured to detect interference light based on light having passed through the signal optical path and returning from the eye, and reference light having passed through the reference optical path; and
an image forming unit configured to form an image of the eye based on a detection result obtained by the interference optical system.
(Aspect 3)
An ophthalmic surgical apparatus comprising:
an observation optical system including a zoom lens system, and configured to observe an eye undergoing surgery through an objective lens;
an illumination optical system configured to illuminate the eye through the objective lens;
an interference optical system having a reference optical path and a signal optical path which leads to the eye through a deflecting member located between the objective lens and the zoom lens system, and configured to detect interference light based on light having passed through the signal optical path and returning from the eye, and reference light having passed through the reference optical path; and
an image forming unit configured to form an image of the eye based on a detection result obtained by the interference optical system,
wherein, in the objective lens, a part where the signal optical path passes through and a part Where an optical path formed by the observation optical system passes through have different refractive properties.
(Aspect 4)
An ophthalmic surgical apparatus comprising:
an observation optical system configured to observe an eye undergoing surgery through an objective lens which is provided with a deflecting member;
an illumination optical system configured to illuminate the eye through the objective lens;
an interference optical system having a reference optical path and a signal optical path which leads to the eye through the deflecting member located in the objective lens, and configured to detect interference light based on light having passed through the signal optical path and returning from the eye, and reference light having passed through the reference optical path; and
an image forming unit configured to form an image of the eye based on a detection result obtained by the interference optical system.
(Aspect 5)
The ophthalmic surgical apparatus according to any one of aspects 1 to 4, wherein the deflecting member is located at a position out of at least one of an optical path formed by the observation optical system and an optical path formed by the illumination optical system.

(Aspect 6)

The ophthalmic surgical apparatus according to any one of aspects 1 to 4, wherein the deflecting member is a beam splitter located in at least one of an optical path formed by the observation optical system and an optical path formed by the illumination optical system.

(Aspect 7)

The ophthalmic surgical app apparatus according to aspect 6, wherein the beam splitter is a dichroic mirror located in the optical path formed by the observation optical system.

(Aspect 8)

The ophthalmic surgical apparatus according to aspect 6, wherein the beam splitter is a dichroic mirror or a half mirror located in the optical path formed by the illumination optical system.

(Aspect 9)

The ophthalmic surgical apparatus according to any one of aspects 1 to 8, wherein a first optical unit, which houses at least part of the interference optical system, is formed as an attachment that is configured to be detachably attached to a main body that holds at least the objective lens.

(Aspect 10)

The ophthalmic surgical apparatus according to aspect 9, wherein the interference optical system includes:

a splitting unit configured to split light from a light source into signal light and reference light, a scanner configured to scan the eye with light guided through the signal optical path, and an interference unit configured to cause the signal light having passed through the signal optical path and returning from the eye to interfere with the reference light having passed through the reference optical path, the deflecting member is located between the scanner and the eye, and the first optical unit houses at least the scanner and the deflecting member.

(Aspect 11)

The ophthalmic surgical apparatus according to aspect 10, further comprising a combining unit configured to combine the signal optical path with an optical path of visible light from a visible light source at a position between the splitting unit and the scanner.

(Aspect 12)

The ophthalmic surgical apparatus according to aspect 10 or 11, wherein the first optical unit further houses an image sensor that is located in an optical path branched from the signal optical path between the scanner and the deflecting member.

(Aspect 13)

The ophthalmic surgical apparatus according to aspect 12, further comprising a scan controller configured to control the scanner based on an image acquired by the image sensor.

(Aspect 14)

The ophthalmic surgical apparatus according to aspect 13, wherein the first optical unit further houses the scan controller.

(Aspect 15)

The ophthalmic surgical apparatus according to any one of aspects 10 to 14, wherein at least part of the interference unit and the splitting unit are housed in a second optical unit, and the first optical unit and the second optical unit are connected by a light guide.

(Aspect 16)

The ophthalmic surgical apparatus according to any one of aspects 9 to 15, wherein the main body is provided with a first connection portion, and the first optical unit is provided with a second connecting portion, when the first connection portion and the second connecting portion are connected to each other, the first optical unit is attached to the main body, and the first connecting portion is configured to be connectable to a third connecting portion of an attachment other than the first optical unit.

(Aspect 17)

The ophthalmic surgical apparatus according to any one of aspects 9 to 16, further comprising a controller configured to control the observation optical system and the illumination optical system, wherein the controller is configured to control the interference optical system when the first optical unit is attached to the main body.

(Aspect 18)

The ophthalmic surgical apparatus according to any one of aspects 1 to 8, wherein a third optical unit houses at least the deflecting member, a fourth optical unit houses at least part of the interference optical system, and the fourth optical unit is configured to be detachably attached to the third optical unit, which is being attached to the main body that holds at least the objective lens.

(Aspect 19)

The ophthalmic surgical apparatus according to any one of aspects 1 to 18, further comprising a mechanism configured to move the deflecting member.

(Aspect 20)

An attachment for ophthalmic surgery, configured to be detachably attached to an ophthalmic surgical microscope that includes an observation optical system configured to observe an eye undergoing surgery through an objective lens, and an illumination optical system configured to illuminate the eye through the objective lens, wherein the attachment comprises a deflecting member, which is located between the objective lens and the eye E in a state of being attached to the ophthalmic surgical microscope, and the attachment is configured to lead a signal optical path from an interference optical system, which has the signal optical path and a reference optical path and detects interference light based on light having passed through the signal optical path and returning from the eye and reference light having passed through the reference optical path, to the eye through the deflecting member.

(Aspect 21)

An attachment for ophthalmic surgery, configured to be detachably attached to an ophthalmic surgical microscope that includes an observation optical system configured to observe an eye undergoing surgery through an objective lens, and an illumination optical system configured to illuminate the eye through the objective lens, wherein the attachment comprises a deflecting member which is located in a predetermined position in a direction perpendicular to an optical axis of the objective lens from periphery of the objective lens in a state of being attached to the ophthalmic surgical microscope, and the attachment is configured to lead a signal optical path from an interference optical system, which has the signal optical path and a reference optical path and detects interference light based on light having passed through the signal optical path and returning from the eye and reference light having passed through the reference optical path, to the eye through the deflecting member.

(Aspect 22)

An attachment for ophthalmic surgery, configured to be detachably attached to an ophthalmic surgical microscope that includes an observation optical system including a zoom lens system and is configured to observe an eye undergoing surgery through an objective lens, and an illumination optical system configured to illuminate the eye through the objective lens, wherein, in the objective lens, a part where a signal optical path passes through and a part where an optical path formed by the observation optical system passes through have different refractive properties, wherein the attachment comprises a deflecting member which is located between the objective lens and the zoom lens system in a state of being attached to the ophthalmic surgical microscope, and the attachment is configured to lead a signal optical path from an interference optical system, which has the signal optical path and a reference optical path and detects interference light based on light having passed through the signal optical path and returning from the eye and reference light having passed through the reference optical path, to the eye through the deflecting member.

The invention claimed is:

1. An ophthalmic surgical apparatus comprising:
an observation optical system configured to observe an eye undergoing surgery through an objective lens;
an illumination optical system configured to illuminate the eye through the objective lens;
an interference optical system having a reference optical path and a signal optical path which leads to the eye through a deflecting member located between the objective lens and the eye, and configured to detect interference light based on light having passed through the signal optical path and returning from the eye, and reference light having passed through the reference optical path; and
an image forming unit configured to form an image of the eye based on a detection result obtained by the interference optical system, wherein
a first optical unit, which houses at least part of the interference optical system, is formed as an attachment that is configured to be detachably attached to a main body that holds at least the objective lens,
the main body is provided with a first connection portion, and the first optical unit is provided with a second connecting portion,
when the first connection portion and the second connecting portion are connected to each other, the first optical unit is attached to the main body, and
the first connecting portion is configured to be connectable to a third connecting portion of an attachment other than the first optical unit.

2. An ophthalmic surgical apparatus comprising:
an observation optical system configured to observe an eye undergoing surgery through an objective lens;
an illumination optical system configured to illuminate the eye through the objective lens;
an interference optical system having a reference optical path and a signal optical path which leads to the eye through a deflecting member located in a predetermined position in a direction perpendicular to an optical axis of the objective lens from periphery of the objective lens, and configured to detect interference light based on light having passed through the signal optical path and returning from the eye, and reference light having passed through the reference optical path; and
an image forming unit configured to form an image of the eye based on a detection result obtained by the interference optical system, wherein
a first optical unit, which houses at least part of the interference optical system, is formed as an attachment that is configured to be detachably attached to a main body that holds at least the objective lens,
the main body is provided with a first connection portion, and the first optical unit is provided with a second connecting portion,
when the first connection portion and the second connecting portion are connected to each other, the first optical unit is attached to the main body, and
the first connecting portion is configured to be connectable to a third connecting portion of an attachment other than the first optical unit.

3. An ophthalmic surgical apparatus comprising:
an observation optical system including a zoom lens system, and configured to observe an eye undergoing surgery through an objective lens;
an illumination optical system configured to illuminate the eye through the objective lens;
an interference optical system having a reference optical path and a signal optical path which leads to the eye through a deflecting member located between the objective lens and the zoom lens system, and configured to detect interference light based on light having passed through the signal optical path and returning from the eye, and reference light having passed through the reference optical path; and
an image forming unit configured to form an image of the eye based on a detection result obtained by the interference optical system,
wherein, in the objective lens, a part where the signal optical path passes through and a part where an optical path formed by the observation optical system passes through have different refractive properties, wherein
a first optical unit, which houses at least part of the interference optical system, is formed as an attachment that is configured to be detachably attached to a main body that holds at least the objective lens,
the main body is provided with a first connection portion, and the first optical unit is provided with a second connecting portion,
when the first connection portion and the second connecting portion are connected to each other, the first optical unit is attached to the main body, and
the first connecting portion is configured to be connectable to a third connecting portion of an attachment other than the first optical unit.

4. An ophthalmic surgical apparatus comprising:
an observation optical system configured to observe an eye undergoing surgery through an objective lens which is provided with a deflecting member;
an illumination optical system configured to illuminate the eye through the objective lens;
an interference optical system having a reference optical path and a signal optical path which leads to the eye through the deflecting member located in the objective lens, and configured to detect interference light based on light having passed through the signal optical path and returning from the eye, and reference light having passed through the reference optical path; and an image forming unit configured to form an image of the eye based on a detection result obtained by the interference optical system, wherein a first optical unit, which houses at least part of the interference optical system, is formed as an attachment that is configured to be detachably attached to a main body that holds at least the objective lens, the main body is provided with a first connection portion, and the first optical unit is provided with a second connecting portion, when the first connection portion and the second connecting portion are connected to each other, the first optical unit is attached to the main body, and the first connecting portion is configured to be connectable to a third connecting portion of an attachment other than the first optical unit.

5. An ophthalmic surgical apparatus comprising:

an observation optical system configured to observe an eye undergoing surgery through an objective lens;

an illumination optical system configured to illuminate the eye through the objective lens;

an interference optical system having a reference optical path and a signal optical path which leads to the eye through a deflecting member located between the objective lens and the eye, and configured to detect interference light based on light having passed through the signal optical path and returning from the eye, and reference light having passed through the reference optical path; and an image forming unit configured to form an image of the eye based on a detection result obtained by the interference optical system; and a controller configured to control the observation optical system and the illumination optical system, wherein a first optical unit, which houses at least part of the interference optical system, is formed as an attachment that is configured to be detachably attached to a main body that holds at least the objective lens, and the controller is configured to control the interference optical system when the first optical unit is attached to the main body.

6. An ophthalmic surgical apparatus comprising:

an observation optical system configured to observe an eye undergoing surgery through an objective lens;

an illumination optical system configured to illuminate the eye through the objective lens;

an interference optical system having a reference optical path and a signal optical path which leads to the eye through a deflecting member located between the objective lens and the eye, and configured to detect interference light based on light having passed through the signal optical path and returning from the eye, and reference light having passed through the reference optical path; and an image forming unit configured to form an image of the eye based on a detection result obtained by the interference optical system, wherein a third optical unit houses at least the deflecting member, a fourth optical unit houses at least part of the interference optical system, and the fourth optical unit is configured to be detachably attached to the third optical unit, which is being attached to the main body that holds at least the objective lens.

7. An ophthalmic surgical apparatus comprising:

an observation optical system configured to observe an eye undergoing surgery through an objective lens;

an illumination optical system configured to illuminate the eye through the objective lens;

an interference optical system having a reference optical path and a signal optical path which leads to the eye through a deflecting member located in a predetermined position in a direction perpendicular to an optical axis of the objective lens from periphery of the objective lens, and configured to detect interference light based on light having passed through the signal optical path and returning from the eye, and reference light having passed through the reference optical path; and an image forming unit configured to form an image of the eye based on a detection result obtained by the interference optical system; and a controller configured to control the observation optical system and the illumination optical system, wherein a first optical unit, which houses at least part of the interference optical system, is formed as an attachment that is configured to be detachably attached to a main body that holds at least the objective lens, and the controller is configured to control the interference optical system when the first optical unit is attached to the main body.

8. An ophthalmic surgical apparatus comprising:

an observation optical system including a zoom lens system, and configured to observe an eye undergoing surgery through an objective lens;

an illumination optical system configured to illuminate the eye through the objective lens;

an interference optical system having a reference optical path and a signal optical path which leads to the eye through a deflecting member located between the objective lens and the zoom lens system, and configured to detect interference light based on light having passed through the signal optical path and returning from the eye, and reference light having passed through the reference optical path;

an image forming unit configured to form an image of the eye based on a detection result obtained by the interference optical system; and a controller configured to control the observation optical system and the illumination optical system, wherein in the objective lens, a part where the signal optical path passes through and a part where an optical path formed by the observation optical system passes through have different refractive properties, a first optical unit, which houses at least part of the interference optical system, is formed as an attachment that is configured to be detachably attached to a main body that holds at least the objective lens, and the controller is configured to control the interference optical system when the first optical unit is attached to the main body.

9. An ophthalmic surgical apparatus comprising:

an observation optical system configured to observe an eye undergoing surgery through an objective lens which is provided with a deflecting member;

an illumination optical system configured to illuminate the eye through the objective lens;

an interference optical system having a reference optical path and a signal optical path which leads to the eye through the deflecting member located in the objective lens, and configured to detect interference light based on light having passed through the signal optical path and returning from the eye, and reference light having passed through the reference optical path; and an image forming unit configured to form an image of the eye based on a detection result obtained by the interference optical system; and a controller configured to control the observation optical system and the illumination optical system, wherein a first optical unit, which houses at least part of the interference optical system, is formed as an attachment that is configured to be detachably attached to a main body that holds at least the objective lens, and the controller is configured to control the interference optical system when the first optical unit is attached to the main body.

10. An ophthalmic surgical apparatus comprising:

an observation optical system configured to observe an eye undergoing surgery through an objective lens;

an illumination optical system configured to illuminate the eye through the objective lens;

an interference optical system having a reference optical path and a signal optical path which leads to the eye through a deflecting member located in a predetermined position in a direction perpendicular to an optical axis of the objective lens from periphery of the objective lens, and configured to detect interference light based on light having passed through the signal optical path and returning from the eye, and reference light having passed through the reference optical path; and an image forming unit configured to form an image of the eye based on a detection result obtained by the interference optical system, wherein a third optical unit houses at least the deflecting member, a fourth optical unit houses at least part of the interference optical system, and the fourth optical unit is configured to be detachably attached to the third optical unit, which is being attached to the main body that holds at least the objective lens.

11. An ophthalmic surgical apparatus comprising:

an observation optical system including a zoom lens system, and configured to observe an eye undergoing surgery through an objective lens;

an illumination optical system configured to illuminate the eye through the objective lens;

an interference optical system having a reference optical path and a signal optical path which leads to the eye through a deflecting member located between the objective lens and the zoom lens system, and configured to detect interference light based on light having passed through the signal optical path and returning from the eye, and reference light having passed through the reference optical path; and an image forming unit configured to form an image of the eye based on a detection result obtained by the interference optical system, wherein, in the objective lens, a part where the signal optical path passes through and a part where an optical path formed by the observation optical system passes through have different refractive properties, wherein a third optical unit houses at least the deflecting member, a fourth optical unit houses at least part of the interference optical system, and the fourth optical unit is configured to be detachably attached to the third optical unit, which is being attached to the main body that holds at least the objective lens.

12. An ophthalmic surgical apparatus comprising:

an observation optical system configured to observe an eye undergoing surgery through an objective lens which is provided with a deflecting member;

an illumination optical system configured to illuminate the eye through the objective lens;

an interference optical system having a reference optical path and a signal optical path which leads to the eye through the deflecting member located in the objective lens, and configured to detect interference light based on light having passed through the signal optical path and returning from the eye, and reference light having passed through the reference optical path; and an image forming unit configured to form an image of the eye based on a detection result obtained by the interference optical system, wherein a third optical unit houses at least the deflecting member, a fourth optical unit houses at least part of the interference optical system, and the fourth optical unit is configured to be detachably attached to the third optical unit, which is being attached to the main body that holds at least the objective lens.

* * * * *